US006613538B2

(12) United States Patent
Librach et al.

(10) Patent No.: US 6,613,538 B2
(45) Date of Patent: Sep. 2, 2003

(54) DETECTION OF HLA-G

(76) Inventors: Clifford L. Librach, 790 Bay Street, Suite 1020, Toronto, Ontario (CA), M5G IN8; Shang-mian Yie, 5 Shady Golfway, #202, North York, Ontario (CA), M3C 3A5

( * ) Notice: Subject to any disclaimer, the term of this patent is extended or adjusted under 35 U.S.C. 154(b) by 0 days.

(21) Appl. No.: 09/813,410

(22) Filed: Mar. 21, 2001

(65) Prior Publication Data

US 2002/0015973 A1 Feb. 7, 2002

Related U.S. Application Data

(63) Continuation-in-part of application No. 09/407,056, filed on Sep. 27, 1999, now abandoned, and a continuation-in-part of application No. PCT/CA00/01116, filed on Sep. 27, 2000, now abandoned.

(51) Int. Cl.[7] ................... G01N 33/543; G01N 33/577; A61B 17/435; C07K 16/20; C12N 5/20
(52) U.S. Cl. ................... 435/7.94; 435/7.21; 435/70.21; 435/452; 435/330; 435/334; 435/344; 436/518; 436/548; 436/906; 530/387.7; 530/388.22; 530/388.8; 530/391.1; 530/853; 600/33; 600/34
(58) Field of Search ................... 435/1.1, 7.21, 435/7.92, 7.93, 7.94, 70.21, 452, 330, 331, 334, 335, 344; 436/501, 518, 548, 63, 64, 65, 813, 814, 906; 530/387.7, 387.9, 388.2, 388.22, 388.23, 388.8, 388.85, 391.1, 851, 853; 600/33, 34

(56) References Cited

FOREIGN PATENT DOCUMENTS

| WO | WO96/31604 | 10/1996 |
|---|---|---|
| WO | WO99/43851 | 9/1999 |
| WO | WO00/29847 | 5/2000 |

OTHER PUBLICATIONS

Fournel, Sylvie et al., "Soluble HLA–G: Purification from Eukaryotic Transfected Cells and Detection by a Specific ELISA"; *American Journal of Reproductive Immunology*, vol. 42, No. 1, Jul. 1999, pp. 22–29.

Jurisicova Andrea et al., "Variability in the expression of trophectodermal markers β–human chorionic gonadotrophin, human leukocyte antigen–G and pregnancy specific β–1 glycoprotein by thr human blastocyst"; *Human Reproduction*, vol. 14, No. 7, Jul. 1999, pp. 1852–1858.

Mallet Valerie et al., "Primary cultured human thymic epithelial cells express both membrane–bound and soluble HLA–G translated products"; *Journal of Reproductive Immunology*, vol. 43, No. 2, Jul. 1999, pp. 225–234.

Cross et al., "Implantation and the Placenta: Key Pieces of the Development Puzzle," Dec. 2, 1994, Science, vol. 266: 1508–1518.

(List continued on next page.)

*Primary Examiner*—Christopher L. Chin
*Assistant Examiner*—James L. Grun
(74) *Attorney, Agent, or Firm*—Price, Heneveld, Cooper, DeWitt & Litton

(57) ABSTRACT

The present invention relates to the detection of HLA-G. Antibodies to both soluble and membrane bound HLA-G are disclosed. Exemplary antibodies include 2C/C8, 3C/G4, and 4H84. 2C/C8 and 4H84 antibodies bind to the same region of HLA-G, which is a different region than that bound by 3C/G4. Methods of detection and diagnosis are disclosed as well as kits, including a miniaturized assay suitable for a clinical setting. Further, a method of selecting an embryos for in vitro fertilization is disclosed. A sandwich ELISA test is provided using two antibodies that bind to HLA-G at different regions. The HLA-G test according to the invention is over 1000 times more selective in binding to HLA-G than to antigens $HLA-A_2$, $HLA-B_4$, HLA-C, or mixed WBC preparations.

7 Claims, 20 Drawing Sheets

OTHER PUBLICATIONS

Sherman, et al., "The Molecular Basis of Allorecognition," (1993), Annu. Rev. Immunol. 11: 385–402.

Geraghty et al., "A Human major histocompatibility complex class I gene that encodes a protein with a shortened cytoplasmic segment:," Proc. Natl. Acad. Sci. U.S.A., vol. 84, pp. 9145–9149, Dec. 1987.

Parham et al., "Nature of polymorphism in HLA–A, –B, and –C molecules," Proc. Natl. Acad. Sci. U.S.A., vol. 85, pp. 4005–4009, Jun. 1988, Immunology.

Shimizu et al., "Transfer and expression of three cloned humna non–HLA–A,B,C class I major histocompatibility complex genes in mutant lymphoblastoid cells," Proc. Natl. Acad. Sci. U.S.A. 85, pp. 227–231, Jan. 1988, Immunology.

Ishitani and Geraghty, "Alternative splicing of HLA–G transcripts yields proteins with primary structures resembling both class I and II antigens," Proc. Natl. Acad. Sci., U.S.A., vol. 89, pp., 3947–3951, May 1992, Immunology.

Kirszenbaum et al.., "An alternatively spliced form of HLA–G mRNA in humna trophoblasts and evidence for the presence of HLA–G transcript in adult lymphocytes," Proc. Natl. Acad. Sci., U.S.A., vol. 91, pp. 4209–4213, May 1994, Immunology.

Fujii et al., A Soluble Form of the HLA–G Antigen is Encoded by a Messenger Ribonucleic Acid Containing Intron 4 (1994) J. Immunol. 153: 5516–5524, Sep. 1994.

Van der Ven and Ober, "HLA–G Polymorphisms in African Americans," J. Immunol. 153:5628–5633, Sep. 1994.

Rochat R.W., et al., "Material Morality in the United States: Report form the Material Mortality Collaborative," Obstet Gynecol, 72(1):91–97.

Redman C.W. Current Topic: Pre–eclampsia and the Placenta, Placenta (1991), 12(4):301–308.

Chun D., et al., Clinical Observations on Some Aspects of Hydatidiform Moles J. Obstet.. Gynecol. Br. Commonw. 1964: 71: 180–184.

Redman C.W.G., "Immunology of Preeclampsia,"Semin Perinatol, vol. 15, Jun. 1991, 15(3):257–62.

Jurisicova A., et al., "Embryonic human leukocyte antigen–G expression: possible implications for human preimplantation development," Fertil. Steril., 65(5):997–1002, May 1996.

Jurisicova A., et al., "HLA–G expression durign preimplantation hyman embryo development," Proc. Natl. Acad. Sci. U.S.A., vol. 93, pp. 161–165, Jan. 1996, Developmental Biology.

Leese H.J., et al., Early human embryo metabolism,: Bioessays, vol. 15(4), pp. 259–264, Apr. 1993.

McMaster M., et al., "Human Placental HLA–G Expression is Restricted to Differentiated Cytotrophoblasts," J. Immunology. 154–3771–3778, 1995.

AbouZahr C., et al, in 1996 Maternal Mortality. World Health Stat Q, 49(2): 77–87.

Redman, C.W.G., "The Immunology of Preclampsia," in Immunology of Pregnancy, edt by Chaout G, CRC press, Boca Raton, pp. 205–230, 1993.

Kupferminc, M.J. et al., "Tumor necrosis factor–$\alpha$ is elevated in plasma and amniotic fluid of patients with severe preeclampsia," Am. J. Obstet. Gynecol. 1994: 170(6): 1752–1759.

Sunder–Plassmann, G. et al., "Increased Serum activity of interleukin–2 in patients with preeclampsia," J. Autoimmunity, 2(2): 203–205, Apr. 1989.

Hara, N. Fuji et al., "Histochemical Demonstration of Interleukin–2 in Decidua Cells of Patients with Preeclampsia," Am. J. Reprod. Immunol. 1995: 34: 44–51.

Hara, N. Fuji et al., "Altered Expression of Human Leukocyte Antigen G (HLA–G) on Extravillous Trophoblasts in Preeclampsia: Immunohistological Demonstration with anti–HLA–G Specific Antibody "87G" and Anti–cytokeratin Antibody 'CAM5.2,'" Am. J. Reprod. Immunol. 1996: 36: 349–358.

Lim, KH et al., "Human Cytotrophoblast Differentiation/Invasion is Abnormal in Preeclampsia," A. J. Pathol. 1997: 151: 1809–1818.

Ellis, Shirley, "HLA G: At the interface," Am. J. Reprod. Immunol. 1990: 23: 84–86.

Loke, Y. W., "Evaluation of trophoblast HLA–G antigen with a specific monoclonal antibody," Tissue Antigen 1997: 50: 135–146.

Kovats, Susan et al., "A Clas I Antigen, HLA–G, Expressed in Human Trophoblasts," Science 1990: 248: 220–223.

Chumbley, Gill et al., "Resistance of HLA–G and HLA–A2 Transfectants to Lysis by Decidual NK Cells," Cell Immunol. 1994: 155: 312–322.

Deniz, Gunnur et al., "Phenotypic and Functional Cellular Difference Between Human CD3–Decidual and Peripheral Blood Leukocytes," J. Immunol. 1994: 152: 4255–4261.

Sanders, S.K. et al., "Cell–Cell Adhesion Mediated by CD8 and Juman Histocompatibility Leukocyte Antigen G, a Nonclassical Major Histocompatibility Complex Class 1 Molecule on Cytotrophoblasts," J. Exp. Med., 1991: 174: 737–740.

Chesley, Leon C., Editorial, "Diagnosis of Preeclampsia," Obstet. Gynecol, Mar. 1985: vol. 65(3): 423–425.

McMaster, Michael et al, "HLA–G Isoforms Produced by Placental Cytotrophoblasts and Found in Amniotic Fluid are Due to Unusual Glycosylation," J. Immunol. 1998: 160: 5922–5928.

Laemmli, U.K, "Cleavage of Structural Proteins during the Assembly of the Head of Bacteriophage T4," Nature—Aug. 15, 1970, vol. 227, pp. 680–685.

Harlow E. Lane D: Monoclonal Antibodies. In Antibodies: a laboratory manual. edt. By Harrow E. and Lane D., Cold Spring Harbor Laboratory, Cold Spring Harbor, NY, pp. 139–149.

Colbern, Gail T. et al., "Expression of the nonclassic histocompatibility antigen HLA–G by preeclampsia placenta," Am. J. Obstet. Gynecol 1994: 170: 1244–1250.

Le Bouteiller, P. et al., "Antigen–presenting function(s) of he non–classical HLA–E, –F and –G class I molecules: the beginning of a story," Res. Immunol. 1996: 147: 301–312.

Crisa, Laura et al., "Identification of a Thymic Epithelial Cell Subset Sharing Expression of the Class Ib HLA–G Molecule with Fetal Trophoblasts," J. Exp. Med. 1997: 186: 289–298.

Omu, Alexander E. et al., "Effect of Antihypertensive Therapy in Preeclampsia on Levels of Serum Interleukin–4," Gynecol. Obstet. Invest. 1996: 42: 230–236.

Clark, David A., Editorial, HLA–G Finally Does Something!, Am. J. Reprod. Immunol. 1997: 38: 75–78.

Maejima, M. et al., "Presence of HLA–G Expressing Cells Modulates the Ability of Peripheral Blood Mononuclear Cells to Release Cytokines," Am. J. Reprod. Immunol., 1997: 38: 79–82.

Rebmann et al., "Detection of soluble HLA–G molecules in plasma and amniotic fluid", Tissue Antigens 53: 14–22, Jan. 1999.

Hellstrom et al., "Monoclonal antibodies for cancer detection and therapy" (Baldwin et al., eds.), Academic Press, London, 1985, p. 20.

Geraghty et al., Production Of Monoclonal Antibodies Specific For The New Class I Antigen HLA–G And Their Use To Examine Expression In Trophoblast Cells, FASEB Journal 4(7): A2216, Abstract #3016, 1990.

DETECTION OF HLA-G

CROSS REFERENCE TO RELATED APPLICATION

This application is a continuation-in-part of U.S. application Ser. No. 09/407,056, filed on Sep. 27, 1999, now abandoned and PCT Ser. No. PCT/CA00/01116, filed Sep. 27, 2000, and now abandoned.

FIELD OF INVENTION

The present invention relates to the detection of HLA-G. The present invention provides antigens for generating specific antibodies to both soluble and membrane bound HLA-G, as well as exemplary antibodies.

BACKGROUND OF THE INVENTION

A central question in pregnancy is how the fetal-placental unit avoids maternal immune rejection. Although fetal and maternal cells interact throughout pregnancy, the fetus typically remains a privileged site, not subject to rejection. It is likely that the particular nature of the cells at the fetal-maternal interface and their products help prevent rejection of the fetus by the maternal immune system.

Implantation and placental development physically connect the mammalian embryo to the maternal uterus. Establishing this connection is essential for subsequent development. The initial developmental events which occur in the embryo set aside unique extraembryonic cellular lineages which are the precursors of the placenta. The first differentiation event gives rise to trophoblasts, which are specialized epithelial cells of the placenta that physically connect the embryo and the uterus, see for example Cross et al. (1994), *Science* 266: 1508 for a review of the events surrounding implantation and formation of the placenta.

After fertilization in the oviduct, a series of cell divisions create a mass of totipotent cells called the morula. The first differentiation event occurs after compaction of the morula, leading to formation of the blastocyst. Cells of the trophoblast lineage are formed based upon their position in the morula in a complex cascade of inter- and intra-cell signaling events. In primates, implantation of the blastocyst occurs shortly after the blastocyst hatches from the zona pellucida.

The uterus is made receptive to implantation as a result of events controlled largely by production of estrogen and progesterone from the ovaries. During implantation, trophoblasts attach to the receptive uterine epithelium initiating several changes in the endometrium. Vascular changes occur, such as increased permeability of uterine blood vessels, and inflammatory cells are recruited to the implantation site. Proinflammatory cytokines are produced in the uterus and several cellular chances occur. For example, the uterine epithelium is lost and decidual cells undergo an epithelioid transition and proliferate, producing a massively thickened uterine wall. The decidua also contains abundant macrophages, lymphocytes and other bone-marrow derived cells with unusual properties such as reduced alloreactivity, and responsiveness to stimulation by CD3 antibody.

After implantation in humans, distinct populations of differentiated trophoblasts form. Proliferative cytotrophoblast stem cells are anchored to basement membranes surrounding a stromal core in two types of chorionic villi. In floating villi, cytotrophoblast stem cells detach from the underlying basement membrane and fuse to form a syncytium, a polynucleate cell, which covers the villus and is in direct contact with maternal blood. In anchoring villi, cytotrophoblast stem cells differentiate, by detaching from their basement membrane and aggregating to form columns of mononuclear cells which attach to and invade the uterine decidua (interstitial invasion) and its arterial system (endovascular invasion). Interstitial invasion puts cytotrophoblasts in direct contact with the highly specialized subset of leukocytes that are home to the uterus during pregnancy. Endovascular invasion puts cytotrophoblasts, like the syncytiotrophoblasts covering the anchoring villi, in direct contact with maternal blood. Thus, antigen presentation by trophoblasts at the maternal-fetal interface is an important component of maternal immunological responses during pregnancy.

MHC class I molecules and the peptides they present regulate alloreactivity, see for example Sherman, at al. (1993), *Annu. Rev. Immunol.* 11: 385. Thus, one key to understanding maternal tolerance of the fetal semi-allograft lies in studying trophoblast expression of class I molecules. The molecule HLA-G, which is expressed by placental cells, was cloned in a search for novel class I genes encoded by the human MHC, see for example Geraghty et al. (1987) *Proc. Natl. Acad. Sci. U.S.A.* 84: 9145. The gene has an intron/exon organization identical to that of the class 1a genes (HLA-A, -B and -C), and the HLA-G protein product has 86% sequence identity to the class I consensus sequence, see for example Parham et al. (1988) *Proc. Natl. Acad. Sci U.S.A.* 85: 4005. HLA-G has a lower molecular mass (37–39 kDa) then class 1a molecules due to a stop codon in exon 6 that results in the deletion of all but 6 amino acids in the cytoplasmic tail, see for example Shimizu et al. (1988) *Proc. Natl. Acad. Sci. U.S.A.* 85: 227. With regard to the 5' flanking region of the gene, the HLA-G promoter has elements (e.g., AP-1, NFkB) similar to sequences found in class 1a genes, but lacks an interferon response element, suggesting novel transcriptional regulatory mechanisms. The primary HLA-G RNA transcript is also differentially spliced; in addition to the full length mRNA, transcripts are produced that lack either exon two, both exons two and three (see for example Ishitani and Geraghty (1992) *Proc, Natl, Acad. Sci. U.S.A.* 85: 3947), or exon four (see for example Kirszenbaum et al. (1994) *Proc. Natl. Acad. Sci; U.S.A.* 91:4209). To what extent these alternatively spliced mRNAs are translated is unclear. A soluble form of HLA-G encoded by an mRNA containing intron 4 was described by Fujii et al. (1994) *J. Immunol.* 153: 5516.

HLA-A, -B and -C are highly polymorphic, but HLA-G appears to exhibit relatively less polymorphism. Immunoprecipitation of HLA-G from 13 individuals and a human choriocarcinoma malignant trophoblast cell line showed identical two-dimensional electrophoretic profiles, suggesting reduced polymorphism at this locus. Genomic and cDNA sequence data also indicate that HLA-G has relatively limited polymorphism. However, there is suggestion that at least in some populations, i.e., African Americans, HLA-G exhibits substantial polymorphism, see for example van der Ven and Ober (1994) *J. Immunol.* 153: 5628. Whether HLA-G is complexed with endogenous trophoblast peptides and how this repertoire is affected by its degree of polymorphism remains to be determined.

HLA-G is not generally expressed in non-pregnant adults, making it a suitable marker for the diagnosis and monitoring of pregnancy, and for detecting cytotrophoblasts from biological fluids. In addition, HLA-G levels in the maternal blood are indicative of the vigor of cytotrophoblast invasion and the corresponding health of the placental-maternal interface. Prior to the work of Fisher et al., as described in International Publication No. WO 96/31604, suitable antibodies to HLA-G had not been obtained, due to the high similarity of HLA-G to class 1a molecules which are expressed in adults.

One complication of pregnancy in which an abnormal maternal immune response to the fetus has been implicated is pre-eclampsia. This condition is characterized by development of the classic triad of hypertension, edema, and proteinuria, usually in the third trimester of pregnancy, and is usually associated with signs of neurologic hyperirritability, which may eventually result in grand mal seizures. This pregnancy complication remains one of the major causes of maternal and perinatal mortality in both North American and the developing world, see for example Rochat R W, et al. (1988) Maternal mortality in the United States: report from the Maternal Mortality Collaborative, *Obstet Gynecol,* 72(1):91–7, and AbouZahr C, et al. (1996) Maternal mortality, *World Health Stat Q,* 49(2):77–87.

Despite extensive research into pre-eclampsia, the underlying cause or causes remain unknown. Evidence accumulated thus far strongly suggests that the causative agent is the placenta, see for example Redman (1991) *Placenta,* 12(4):301–8.

Pre-eclampsia can occur with hydatidiform mole or choriocarcinoma, see for example Chun D, et al. (1964) *J. Obstet. Gynecol. Br. Commonw.* 71:180–184, where no fetus is present. The only cure for this widely occurring and life threatening disease is delivery of the placenta. Elucidating the exact role played by the placenta in this disease has been difficult because fundamental aspects of the normal biology of this interesting organ are not well understood. The commonly associated finding of incomplete cytotrophoblast invasion of the spiral arteries suggests impairment of placentation, see for example Lim et al. (1997) *Am. J. Pathol.,* 151(6):1809–18. This lack of trophoblast invasion in pre-eclampsia could be either a primary event or a secondary response to an abnormal immune reaction to the fetus. Several features of this disease suggest that an abnormal response of the mother to the fetus may be the basic defect in this disease, see for example Redman (1991) *Semin Perinatol,* 15(3):257–62. Pre-eclampsia is most likely to occur in primagravidas, and is usually less severe or absent in subsequent pregnancies, but it may reoccur in the same mother if she changes sexual partners. This suggests that an inappropriate response to some paternally derived antigen, possibly HLA-G, may result in pre-eclampsia.

HLA-G expression has been found to be decreased in the placental bed of women with pre-eclampsia, see for example Hara N, et al (1996) *Am J. Reprod. Immunol.,* 36(6):349–58. However, there is currently no good predictive test for the development of pre-eclampsia, even though shallow invasion in the first trimester sets up conditions for the clinical signs that manifest later in pregnancy, most commonly late in the third trimester.

Although International Publication No. WO 96/31604 (Fisher et al.) teaches the formation of anti-HLA-G monoclonal antibodies 1B8 and 3F6, for use in the detection of HLA-G, there is no suggestion that these antibodies be used in the detection of pre-eclampsia. Both of these antibodies bind to a subsequence in the a1 domain of HLA-G. Because these antibodies detect the same region of HLA-G, there is no synergy to be derived from their combined use in detecting HLA-G. There is a need for an improved detection method for HLA-G in which more than one antibody is used, and in which the antibodies used do not compete for the same binding region. Further, there is a need for an HLA-G detection method, such as an ELISA which has a high binding selectivity for HLA-G and low binding selectivity for $HLA-A_2$, $HLA-B_4$, HLA-C and WBC.

Conventional methods for diagnosing pre-eclampsia or for detecting antigens in a biological sample require such a sample to be sent away to a laboratory for analysis, and do not allow rapid detection in a clinical setting.

SUMMARY OF INVENTION

It is object of the present intention to provide an improved test for the measurement of HLA-G in serum levels.

It is another object to provide antigens by generating specific antibodies to both soluble and membrane bound HLA-G.

It is yet a further object of the invention to provide specific antibodies to HLA-G.

It is still a further object of the invention to provide an improved diagnostic test for pre-eclampsia.

Another object of the invention is to provide a miniaturized detection assay, conducive to obtaining rapid results in a clinical setting.

A method is provided for the purification of naturally occurring of HLA-G from human placenta. The method uses any one of the antibodies 3C/G4, 2C/C8, and 4H84.

The invention provides hybridoma 2C/C8, deposited with the International Depositary Authority of Canada (IDAC), Health Canada, 1015 Arlington St., Winnipeg, Manitoba, R3E 3R2 Canada as Accession Number: IDAC 130900-1, deposited on September 13, 2000. This hybridoma produces 2C/C8 antibodies, and is deposited in accordance with all aspects of the Budapest Treaty.

The invention also provides hybridoma 3C/G4, also deposited with the International Depositary Authority of Canada (IDAC). Hybridoma 3C/G4 was afforded Accession Number: IDAC 130900-2, deposited on September 13, 2000. This hybridoma produces 3C/G4 antibodies, and is deposited in accordance with all aspects of the Budapest Treaty.

It has been found that the monoclonal antibody 2C/C8 for HLA-G has substantially the same binding site an the monoclonal antibody 4H84.

The invention provides a method for detecting HLA-G in a biological sample comprising the steps of: (a) depositing a biological sample on a support having an immobilized anti-HLA-G antibody bound thereto, wherein the immobilized anti-HLA-G antibody binds to a first region of HLA-G; (b) contacting the support having the biological sample deposited thereon with an HLA-G label, wherein the label binds to a second region of HLA-G; and (c) detecting the label. In an optional embodiment of the invention, the immobilized anti-HLA-G antibody is 2C/C8, 3C/G4 or 4H84.

Further, the invention relates to a method for identifying an HLA-G indicative condition in a patient comprising the steps of obtaining a biological sample from the patient, followed by the above-noted method for detecting HLA-G.

The invention also provides a method for determining potential for successful implantation of an embryo comprising the steps of obtaining a sample of a fluid medium incubating the embryo followed by the above-noted method for detecting HLA-G.

According to the invention, there is provided a kit comprising: (a) a support having an immobilized anti-HLA-G antibody bound thereto; wherein the immobilized anti-HLA-G antibody binds to a first region of HLA-G; and (b)

an HLA-G label which binding to a second region of HLA-G. According to an optional embodiment of the invention, the HLA-G label comprises a mobile anti-HLA-G antibody having a reporter molecule bound thereto. The reporter molecule may be any molecule which is detectable in a quantitative or nearly quantitative manner. For example, a reporter molecule may be a calorimetric agent, a fluorometric agent, a radioisotope, or an enzymatic agents having a detectable end-point.

By the term "mobile" as it is used herein with respect to a mobile anti-HLA-G antibody, it is merely indicating that the antibody is not bound to the support, unlike the immobilized antibody, which is bound to the support. Of course, the mobile antibody may be bound to other molecules, such as the reporter molecule. The mobile antibody may be provided in any manner known in ELISA technology, such as in a fluid solution.

When the HLA-G label is a mobile anti-HLA-G antibody having a reporter molecule bound thereto, an optional embodiment of the invention is provided as follows. The immobilized anti-HLA-G antibody may be consisting of 2C/C8, 3C/G4 or 4H84. The mobile anti-HLA-G antibody is then either 2C/C8, 3C/G4, or 4H84, provided that the mobile and immobilized antibodies bind to different regions of HLA-G, referred to herein as a "first region" and a "second region". In this way, there is no competitive binding between the mobile and immobilized antibodies. Since 2C/C8 and 4H84 bind to the same region of HLA-G, in this embodiment, either the immobilized anti-HLA-G antibody or the mobile anti-HLA-G antibody is 3C/G4. For example, if the immobilized anti-HLA-G antibody is 2C/C8 or 4H84, the mobile anti-HLA-G antibody is 3C/G4. Conversely, if the immobilized anti-HLA-G antibody is 3C/G4, the mobile anti-HLA-G antibody is either 2C/C8 or 4H84.

The method according to the invention may optionally comprise the step of measuring HLA-G by comparing the quantity of label detected in the biological sample with an HLA-G standard. One possible source of the HLA-G standard is that obtained from a human placenta.

The method according to the invention involves a biological sample. Such a sample may be selected from, but is not limited to amniotic fluid, a medium contacting an embryo, a tissue sample, a blood sample, a medium contacting a tissue sample, and a medium contacting a cell, for example when isolated cells are used.

The inventive method may be used to diagnose or detect an HLA-G indicative condition. In this embodiment, a control value for an HLA-G indicative condition can be compared with the quantity of HLA-G found in the sample. Certain conditions may be indicated if HLA-G is low or absent, while others may be indicated by increased levels of HLA-G. One of skill in the art could easily determine the indicative levels useful in diagnosing a condition. Such HLA-G indicative conditions may include, but are not limited to pre-eclampsia, increased risk of pre-eclampsia, adverse fetal outcome, increased risk of adverse fetal outcome, cancer, or increased risk of cancer development.

Hybridomas 2C/C8 and 3C/G4, both deposited at the International Depositary Authority of Canada on Sep. 13, 2000 and having IDAC Accession Numbers IDAC 130900-1 and 130900-2 are encompassed by the invention. Antibodies produced by these hybridomas, ELISAs involving these antibodies also fall within the scope of the invention.

The method according to an embodiment of the invention may comprise a miniaturized assay conducted on a chip. A chip may refer to a support formed of any plastic or inert polymer such as polystyrene, a cellulose or nitrocellulose support, a silicon-based or metal-based support, or any other platform as is known in the art. According to one embodiment of the invention, an immobilized anti-HLA-G antibody is bound to a polystyrene chip, sized to receive a sample volume ranging from about 5 to 50 $\mu$l. A miniaturized assay can be conducted in a clinical setting, for example for determining HLA-G in a sample of embryo culture medium, for predicting successful embryo implantation. Larger or smaller sample volume assays are also within the scope of the invention, but this embodiment is conducive to an on-site test which does not require a sample to be sent away for laboratory analysis. Use of such a chip, for example within a kit would be advantageous for determining potential for successful implantation of an embryo in in vitro fertility procedures.

The invention further provides a method for selecting an embryo for in vitro fertilization (IVF) comprising the steps of detecting soluble HLA-G secreted by an embryo into an incubation medium, and choosing an embryo secreting soluble HLA-G at a minimum level of 0.01 $\mu$g/ml of incubation medium. Optionally, this method may be combined with the evaluation of embryo cleavage rate, and based on both parameters, an embryo is chosen for IVF. In this method for selecting an embryo, the step of detecting soluble HLA-G may be conducted according to the method for detecting HLA-G according to the invention.

Unless defined otherwise, all terms used herein have the same meaning as commonly understood by one of ordinary skill in the technical art to which this invention belongs. Although methods and materials similar or equivalent to those described herein can be used in the practice or testing of the invention, the preferred methods and materials are described.

The term "antibody" refers to a polypeptide substantially encoded by an immunoglobulin gene or immunoglobulin genes, or fragments thereof. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin, antibody, structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about, for example, 100 or more amino acids primarily responsible for antigen recognition. The terms variable light chain ($V_L$) and variable heavy chain ($V_H$) refer to these light and heavy chains respectively.

Antibodies can exist, for example, as intact immunoglobulins or as a number of well characterized fragments produced by digestion with various peptidases.

Pepsin digests an antibody below the disulfide linkages in the hinge region to produce F(ab)'$_2$, a dimer of Fab which itself is a light chain joined to $V_H$–$C_H$1 by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially an Fab with part of the hinge region broken. While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies.

The term "biological sample or fluid" refers to material derived from a living organism, including but not limited to blood and blood derivatives, cervicovaginal secretions, amniotic fluid, cord blood, urine, tissues, bones and cells.

The term "blood sample" as used herein includes whole blood or derivatives of whole blood well known to those of skill in the art. Thus a blood sample includes the various fractionated forms of blood such as plasma or serum and whole or fractionated blood which additionally comprises various diluents as may be added to facilitate storage or processing in a particular assay. Such diluents are well known to those of skill in the art and include various buffers, anticoagulants, preservatives and the like.

The term "HLA-G" refers to human leukocyte antigen G and unless otherwise stated includes both the soluble and insoluble forms. The term may in appropriate context refer to either the antigen or the genetic locus.

The term "immunoassay" is an analysis or methodology that utilizes an antibody to specifically bind an analyte. The immunoassay is characterized by the use of specific binding properties of at least one particular antibody to isolate, target, or quantify the analyte.

The terms "isolated", "purified", or "biologically pure" refer to material which is substantially or essentially free from components which normally accompany it as found in its native state.

The term "nucleic acid" refers to a deoxyribonucleotide or ribonucleotide polymer in either single- or double-stranded form, and unless otherwise limited, encompasses known analogues of natural nucleotide that can function in a similar manner as naturally occurring nucleotides, for example, incorporating conservative substitutions as is well known in the art.

The term "nucleic acid probe" refers to a molecule which binds to a specific sequence or subsequence of a nucleic acid. A probe is preferably a nucleic acid which binds through complementary base pairing to the full sequence or to a subsequence of a target nucleic acid. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

A "label" is a composition detectable by spectroscopic, photochemical, biochemical, immunochemical, or chemical means. For example, useful labels include $^{32}P$, fluorescent dyes, electron-dense reagents, calorimetric, enzymes, for example, as commonly used in ELISA, biotin, dioxigenin, or haptens and proteins for which antisera or monoclonal antibodies are available can be made detectable.

A "labeled nucleic acid probe" is a nucleic acid probe that is bound, either covalently, through a linker, or through ionic, van der Waals or hydrogen bonds to a label such that the presence of the probe may be detected by detecting the presence of the label bound to the probe.

The term "recombinant" when used with reference to a cell indicates that the cell contains nucleic acid with an origin exogenous to the cell. Thus, for example, recombinant cells replicate and/or express genes that are not found within the native (non-recombinant) form of the cell.

The term "identical" in the context of two nucleic acid or polypeptide sequences refers to the residues in the two sequences which are the same when aligned for maximum correspondence.

The phrases "specifically binds to", "specifically hybridizes to" or "specifically immunoreactive with", when referring to an antibody indicate a binding reaction which is determinative of the presence of the protein in a heterogeneous population of proteins and other biological substances. Thus, under designated immunoassay conditions, the specified antibodies bind preferentially to a particular protein and do not bind in a significant amount to other proteins present in a biological sample or fluid. Specific binding to a protein under such conditions requires an antibody that is selected for its specificity of binding with a particular protein.

Herein, a particular antibody and the cell which produces the antibody may be referred to by the same term, however, one of skill in the art can easily distinguish whether it is the antibody or the cell to which any particular instance pertains. Thus, a hybridoma cell line may be referred to by the name of its defining antibody.

BRIEF DESCRIPTION OF THE DRAWINGS

The invention will be described in more detail in the following way by way of example only and with reference to the attached drawings wherein.

DETAILED DESCRIPTION OF THE INVENTION

Figure 1:
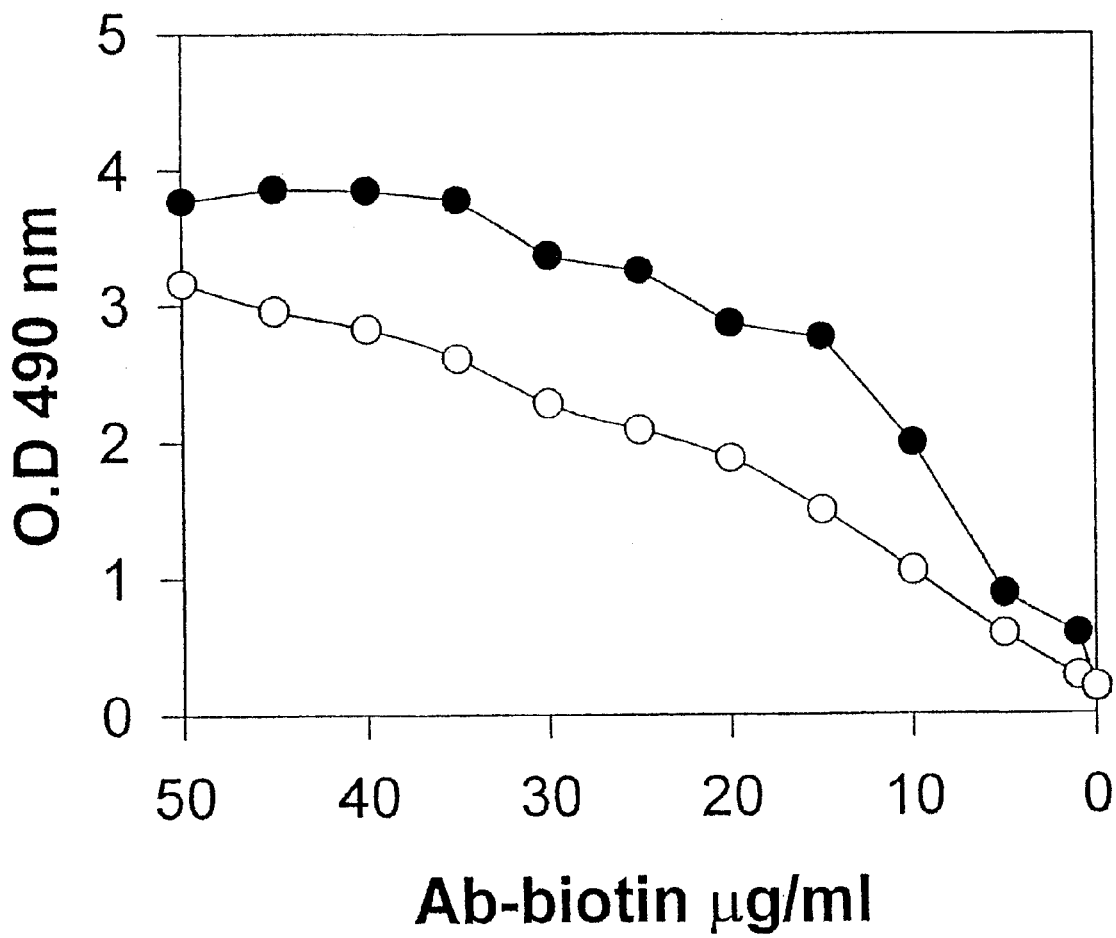
FIG. 1 shows binding affinities of 2C/C8 (o) and 3C/G4 (●) antibodies to HLA-G.

An ELISA has been developed for measurement of serum levels of HLA-G. Using this ELISA, it has been found that women diagnosed with pre-eclampsia had significantly lower levels of HLA-G than normal controls. In addition, it has been found that levels of HLA-G per mg of placental protein were lower in these patients and there was a linear correlation between HLA-G levels in serum and placental tissue of the same woman. This finding leads the way to test women earlier in pregnancy for the presence of HLA-G in their serum. Testing women early in pregnancy for the presence of HLA-G in their serum provides a screening/predictive test for pre-eclampsia.

A critical period of fetal development for survival is that of the early pre-implantation embryo and therefore determining whether HLA-G is expressed during this period is important for understanding its possible role as an embryo protectant. Jurisicova A., et al. (*Fertil. Steril.* (1996) 65(5):997–1002) reported that it is possible to detect HLA-G heavy chain mRNA in 40% of blastocysts, in some embryos at earlier pre-blastocyst cleavage stages of development (2–4 cell, 5–8 cell, and morula) and in some unfertilized oocytes. In concordance with mRNA data, a similar proportion of embryos stained positive for HLA-G immunohistochemistry (Jurisicova, A., et al. (996) *Proc. Natl. Acad. Sci. USA.* 93:161–165). In addition, it was also found that patients who became pregnant and did not have a fetal loss, had a significantly higher proportion of HLA-G positive sibling blastocysts than patients who did not conceive. These studies represented the first report demonstrating the presence of protein and mRNA for the heavy chain of HLA-G, a non-classical class I MHC antigen, and for β2m throughout the whole course of human pre-implantation development from the oocyte to blastocyst stages.

Currently, in vitro fertility (IVF) laboratories are able to select pre-embryos only on the basis of their morphology and rate of in vitro cleavage during the first 48 to 72 hours after fertilization. These criteria are useful, but not always good indicators of developmental potential. In most cases, 3 or 4 embryos are chosen based on these relatively crude indicators and then transferred into the uterine cavity. If additional, more stringent pre-embryo selection criteria were available, based on biochemical, genetic or developmental parameters, it would be possible to transfer one or two healthy pre-embryos, which have the highest chance of survival, without exposing patients to the psychological trauma caused by recurrent embryo implantation failure, spontaneous abortions, multiple IVF trials or the risk of multiple pregnancy. Therefore, a more predictive test for successful implantation would be invaluable.

In addition to the aforementioned utility for a selective HLA-G test, there are other possible utilities. A determination of HLA-G levels in serum is also believed to be indicative of cancer. Cancer cells mask themselves by producing protein indicative of normal cells. In this regard, a selective HLA-G test would be desirable.

Preparation of Monoclonal Antibodies Against HLA-G.

Two hybridoma cell lines named 2C/C8 and 3C/G4 that produce monoclonal antibodies against HLA-G have been made. The hybridomas are deposited with IDAC as Accession Numbers IDAC 130900-1 and 130900-2, respectively. The cell lines were obtained by using purified HLA-G protein to immunize three week old female BALA/c mice according to the procedure described by Harlow Ed and lane D: *Antibodies, a Laboratory Manual,* Cold Spring Laboratory; NY, 1988, which reference is incorporated herein in its entirety. By using a mouse antibody typing kit (Amersham™) the subtype of monoclonal antibody produced by 3C/G4 cell line is determined to be $IgG_3$ while monoclonal antibody secreted by 2C/C8 cell line is determined to be Ig A.

FIG. 1 illustrates binding affinity of 2C/C8 (o) and 3C/G4 (●) antibodies to HLA-G. The 3C/G4 antibody has a higher affinity than 2C/C8 antibody, so that advantageously, 3C/G4 may be used as a first primary antibody and $2C/C_8$ may be used as a second primary antibody in a sandwich ELISA system in accordance with an embodiment of the present invention.

To obtain the antibodies, the cell lines are cultured in a hybridoma culture medium constructed with 410 ml Optimen™ medium (Gibco™), 5 ml TANGOO™ (Sigma™), 0.5 ml ITS (Sigma) and 75 ml FBS (Sigma) for 7 to 10 days until all hybridoma cells die. The debris is removed by centrifugation at 400 g for 10 minutes and supernatant is pooled. The purification of the antibodies is carried out by using a protein G column (Sigma) according to the procedure described by Yie S. M., in *Purification of HLA-G, a Laboratory Manual;* 1997, which reference is incorporated herein in its entirety. The purified antibodies were then concentrated by using a molecular weight 10,000 cut-off filter (Millipore™) and centrifugation at 3000 rpm for 30 minutes at 4° C. Antibodies were stored at −80° C. until use. Antibody yields were approximately 10 μg/ml supernatant.

Figure 2:
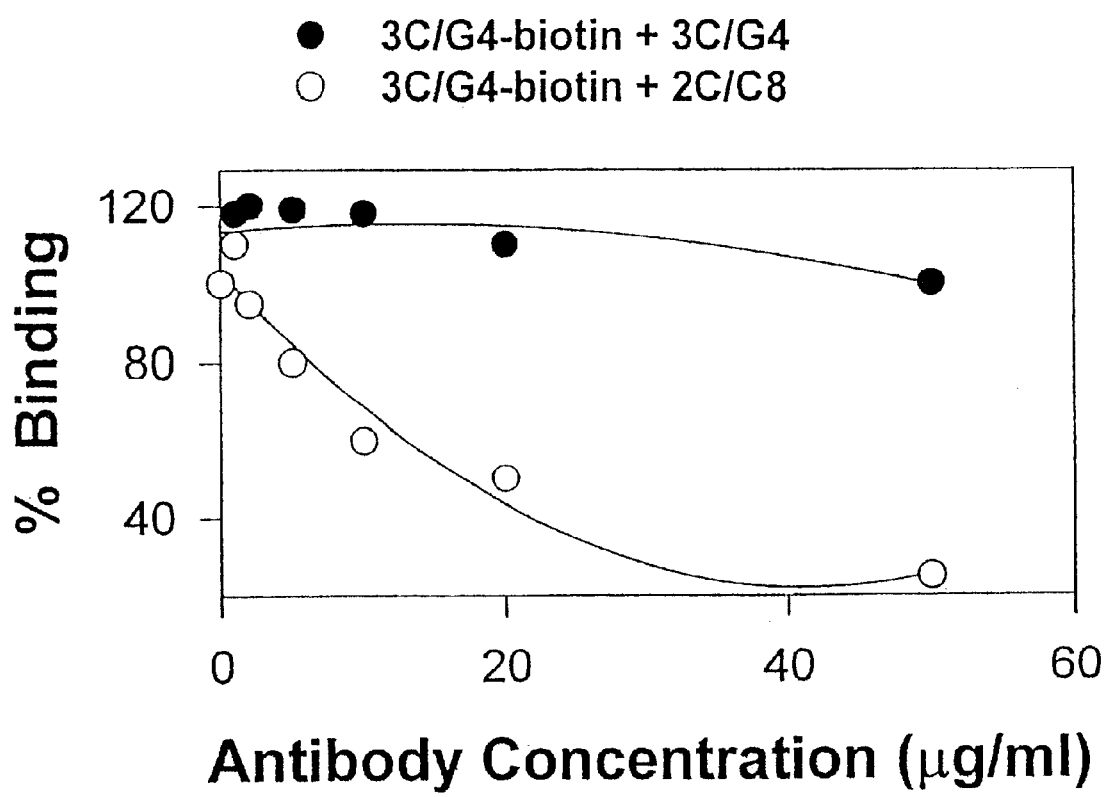
FIG. 2 shows an antibody competition assay for 3C/G4 and 2C/C8.

FIG. 2 illustrates an antibody competition assay for 3C/G4 and 2C/C8. By using a competition antibody capture assay it is demonstrated that the two antibodies bind different binding epitopes of HLA-G molecule.

Specific antibodies were measured by three different approaches, i.e., immunocytochemistry, western blot and ELISA. The antibodies can specifically stain cytotrophoblasts isolated from human first trimester placenta while a negative stain was found in human white blood cell slides, see for example McMaster M et al. (1995) *J. Immunology* 154:3771.

Figure 3A:
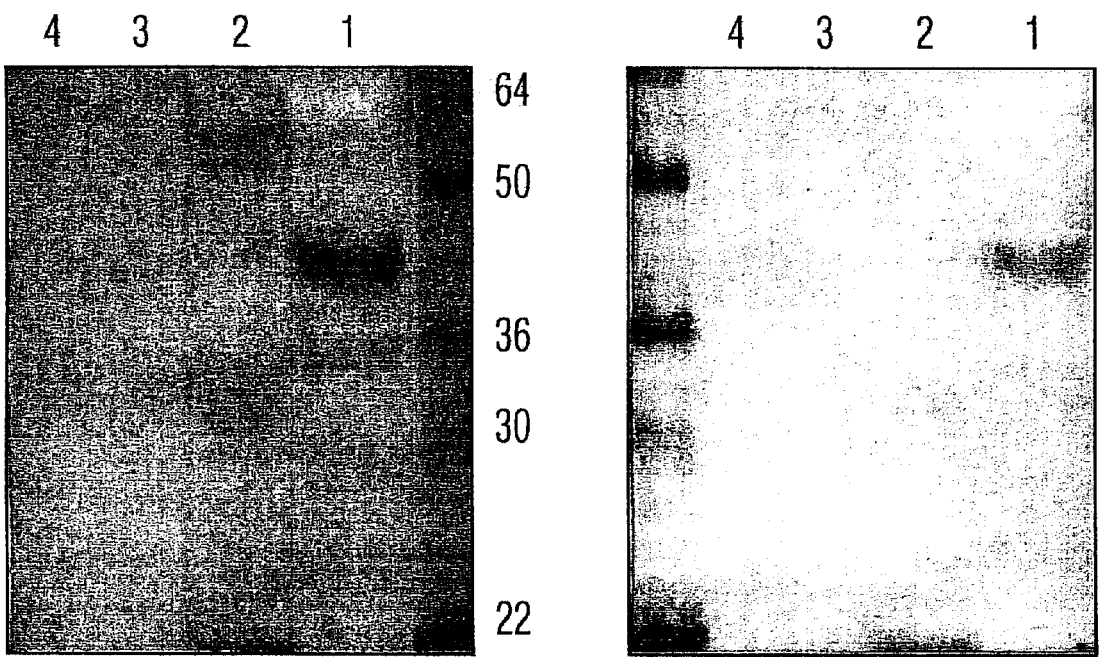
FIG. 3A shows western blotting of some ELISA antibodies, 4H84 and 3C/G4, for HLA-G.

FIG. 3A shows western blotting of some ELISA antibodies, 4H/84 and 3C/G4, for HLA-G. Results are shown in lane 1 for JEG-3, lane 2 shows WBC, lane 3 shows LCL, and lane 4 shows C1R.

Figure 3B:
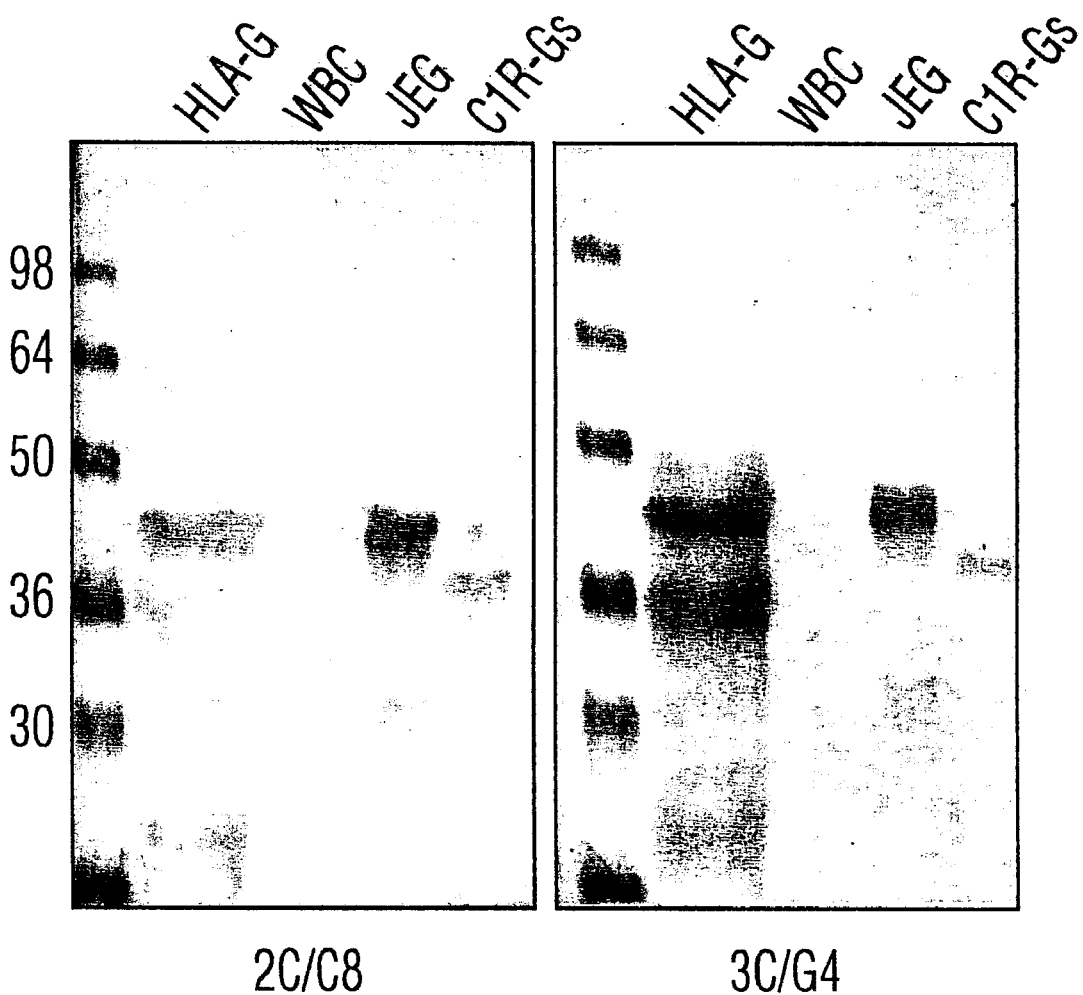
FIG. 3B shows western blotting of some ELISA antibodies, 2C/C8 and 3C/G4, for HLA-G.

FIG. 3B shows western blotting of some ELISA antibodies, 2C/C8 and 3C/G4, for HLA-G. Results are shown in lane 1 for HLA-G, lane 2 shows WBC, lane 3 shows JEG, and lane 4 shows C1R-Gs. Western blotting clearly shows that the antibodies only blot HLA-G.

Table 1 shows that there is no cross reaction of the inventive antibodies with other classical HLA class I antigens, as determined by antigen capture ELISA. These data further confirm the specificity of the inventive antibodies for HLA-G.

TABLE 1

Cross Reactions of 3C/G4 and 2C/C8 Antibodies

| Compounds | Cross-activity % |
| --- | --- |
| HLA-G | 100 |
| HLA-$A_2$ | 0.01 |
| HLA-$B_4$ | 0.01 |
| HLA-C | 0.001 |
| Mixed WBC | 0.005 |

Labeling Biotin to 3C/G4 Antibody. For technical directions for a general procedure the reader is directed to Wilchek M., et al. (1988) *Anal Biochem* 171: 1, which reference is incorporated herein in its entirety.

The purified antibody (2 mg/ml) was extensively dialyzed against 0.1 M PBS/0.15 M NaCl (saline) buffer (pH=7.2) for 24 hours at 4° C. Buffer was changed at least three times during the dialysis. 1 mg of biotin (Sigma™) was dissolved in 30 μl of DMSO (Sigma™) and 70 μl of 0.1 M PBS/saline buffer was then added. The antibody solution was immediately mixed with 38 μl of biotin solution on an end-over-end rocker for 2 hours at room temperature. Unlabeled biotin was separated by using a Sephadex™-25 column (P-10 column, Pharmarcia™) and eluted by 0.01 M PBS buffer (pH=7.2), at a volume of 1 ml per fraction. The presence of antibody-biotin conjugate in each fraction was checked by using Bio-Rad™ protein assay kit. The fractions with high concentration of antibody-biotin conjugate were pooled. Aliquots of the conjugate was stored at −80° C. until use.

Table 2 provides buffer formulations used in the labeling procedure.

TABLE 2

| Buffer Formulations | |
| --- | --- |
| 0.1M PBS/saline | 68 ml of 1M $Na_2HPO_4$, 32 ml of 1M $Na_2HPO_4$, and 8.8 g NaCl. Add dd$H_2O$ to 1 L |
| 0.01M PBS | 6.8 ml of 1M $Na_2HPO_4$, and 3.9 ml of 1M $Na_2HPO_4$. Add dd$H_2O$ to 1 L |

Labeling Horse-Radish Peroxidase (HRP) to 2C/C8 Antibody. For technical directions for a general procedure the reader is directed to Hashida S., et al. (1984) *J Applied Biochemistry* 6:56, which reference is incorporated herein in its entirety. To digest antibody to F(ab)$_2$, the following procedure was followed. 3 mg of antibody purified by G-protein chromatography and eluted with 0.1 M glycine-HCl buffer (pH=3.0) was digested with 60 μg of pepsin (Sigma™) at 37° C. for 16 hours. The enzyme activity was stopped by adjusting pH to 8.0 with 1 N NaOH. A P-100 (Bio-Rad™) gel filtration column (1×50 cm) was used to purify the digested F(ab)$_2$ eluted with 0.1 M PBS buffer (pH=6.0). Fractions with F(ab)$_2$ (MW=4,600) were pooled and concentrated using filter centrifugation.

The introduction of a thiol group to F(ab)$_2$ was conducted as follows. 1 ml F(ab)$_2$ solution was mixed with 0.1 ml of 1 M 2-mercaptoethylamine (Sigma™) in 0.1 M PBS with 5 mM EDTA and incubated at 37° C. for 2 hours. The mixture was purified on a P-10 column, eluted with 0.1 M PBS (pH=6.0) and concentrated by filter centrifugation.

To introduce a maleimide group to HRP, the following procedure was used. 5 mg HRP was dissolved in 0.1 M PBS/0.1 M NaCl/0.1% BSA. Subsequently, 2.6 mg of SSC was dissolved in 0.075 ml NN-dimethylformamide. The HRP solution was incubated with SSC solution at 4° C. overnight. The HRP-maleimide was purified on a P-10 column and concentrated by filter centrifugation.

Conjugation of HRP to F(ab)$_2$ was conducted as follows. 1 mg of HRP-maleimide was incubated with 1.2 mg of thiol F(ab)$_2$ in 0.1 M PBS (pH=6.0) with 5 mM EDTA at 4° C. for 20 hours. The resulting F(ab)$_2$-HRP conjugation was purified on P-100 column.

Figure 4:
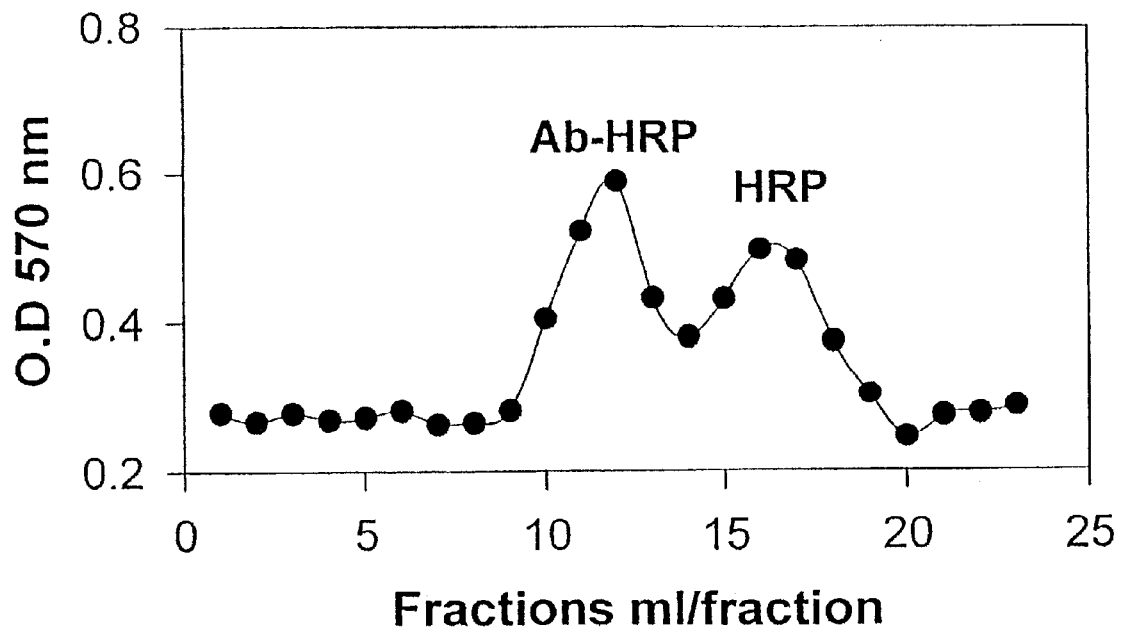
FIG. 4 shows separation of an antibody-HRP conjugate from uncoupled HRP by P-100 gel filtration chromatography.

FIG. 4 shows a purification profile of the F(ab)$_2$-HRP conjugate, illustrating fractional separation of an antibody-HRP conjugate from uncoupled HRP by P-100 gel filtration chromatography.

Figure 5:
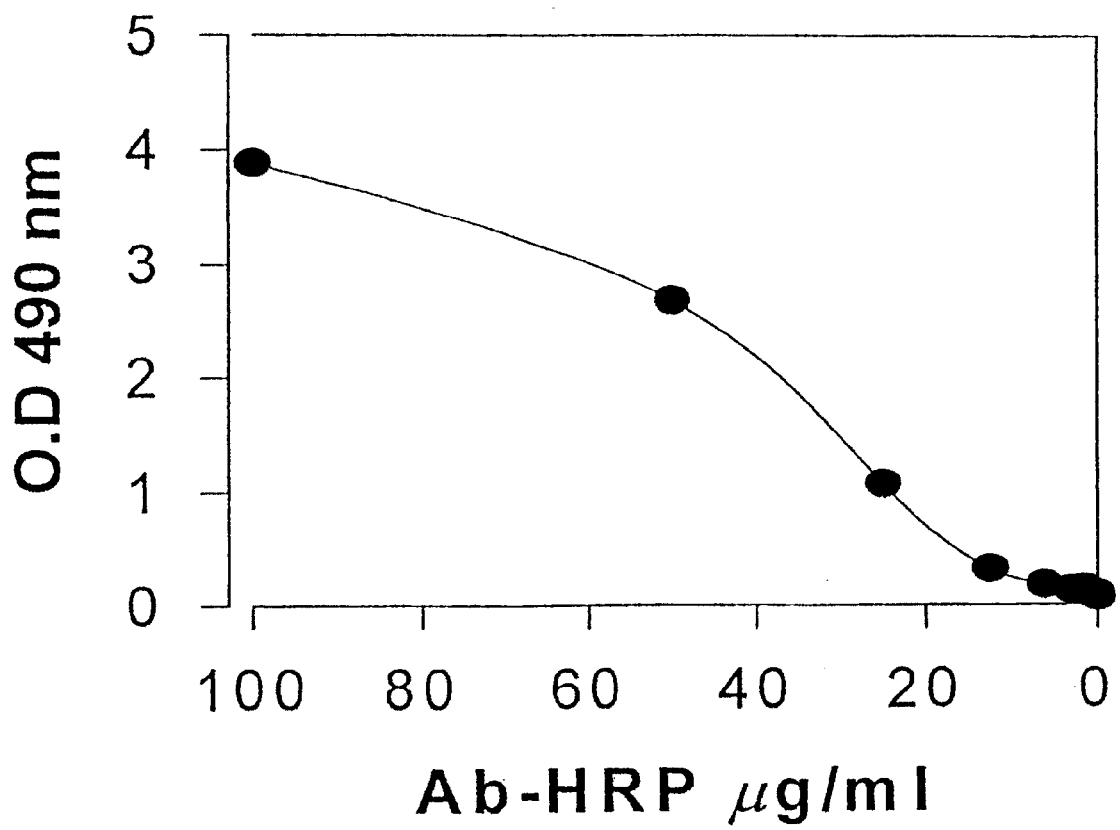
FIG. 5 shows immune and enzyme activity of an antibody-HRP conjugate.

FIG. 5 illustrates the immunological and enzyme activity of the antibody-HRP conjugate obtained in the purification shown in FIG. 4. 100 μl/well of placenta cell lysate was first coated on an ELISA plate. Various concentrations of Ab-HRP conjugate were incubated at 4° C. overnight. Enzyme activity was determined by o-phenylenedianine (OPD) color reaction at 490 nm. The method of assaying a bound HLA-G that is labeled may be selected from many different forms of detection, for example it is possible to assess bound HLA-G by detection with a standard streptavidin-HRP/o-phenylenediamine substrate colour reaction in an ELISA plate reader.

Coating Microplates. In this assay system an indirect coating method was used. A comparison of assay sensitivity between direct and indirect coating antibody showed that indirect coating increased assay sensitivity.

Figure 6:
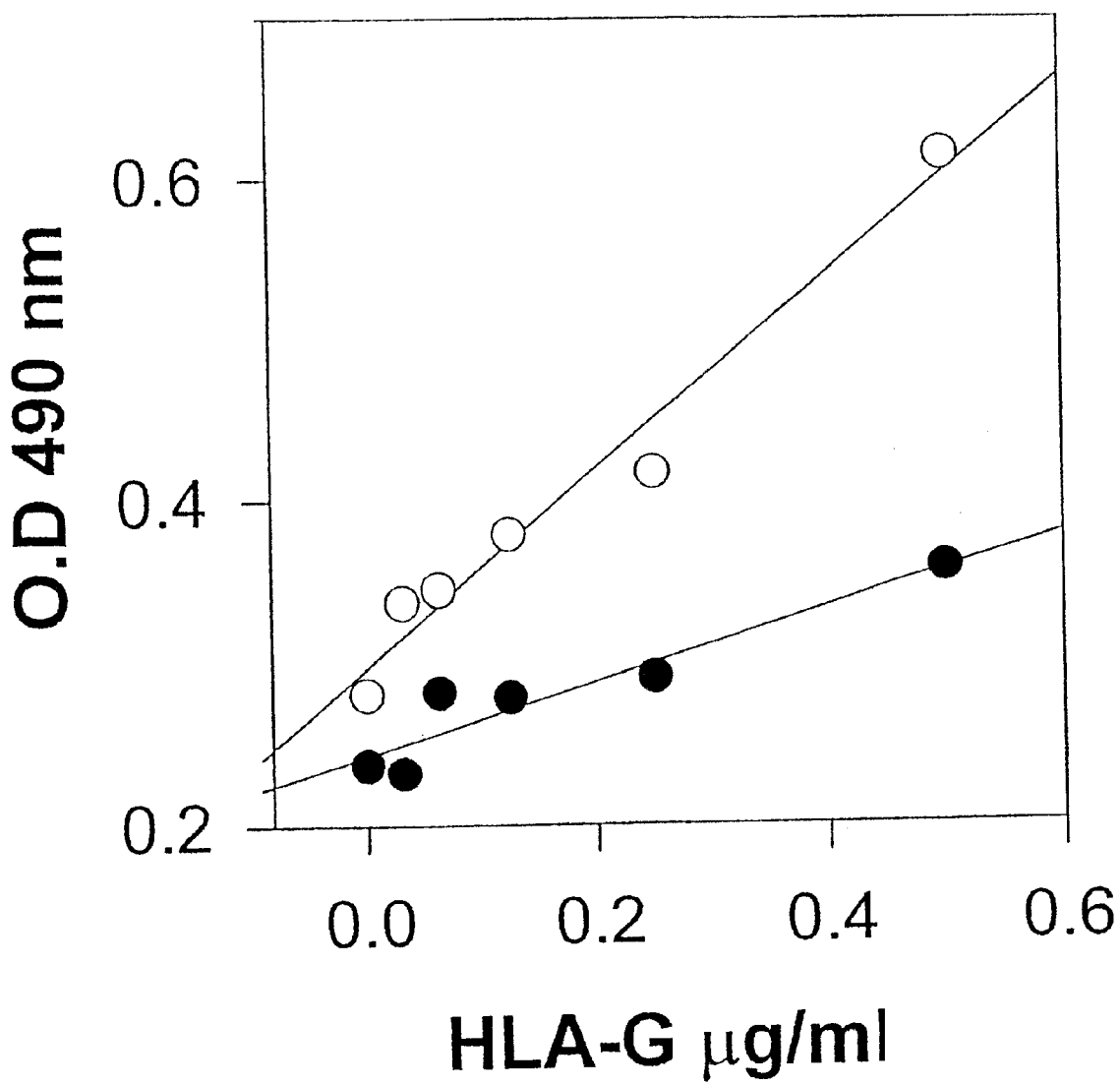
FIG. 6 shows a comparison of standard curves between a direct and an indirect coat antibody.

FIG. 6 shows a comparison of standard curves between direct coating and indirect coating of antibody. Direct coating is shown with a closed circle (●), and indirect coating is shown with an open circle (○). For direct coating, Y=0.243+0.226X, r=0.943; for indirect coating, Y=0.297+0.61X, r=0.984. A 96 well ELISA microplate (Nuc) with high binding capacity was selected. 100 μl of 2 μg/ml to streptoavidin (Sigma™) in 0.1 M $Na_2HCO_3$ buffer (pH=8.0) was first coated on each well at 4° C. overnight. The plate was washed three times with a washing solution. The plate was blocked with 1% BSA in 0.1 M $Na_2HCO_3$ buffer at room temperature for 3 to 4 hours. The block solution was decanted and dried. 100 μl of 3C/G4-biotin conjugate (5 μg/ml) was added to each well and incubated at 4° C. overnight. The plate was washed again with washing solution. The plate was blocked again with 1% BSA in the $Na_2HCO_3$ buffer at room temperature for 3 to 4 hours. The block solution was decanted and dried. Coated plates were effective for at least one month when stored at 4° C.

Figure 7:
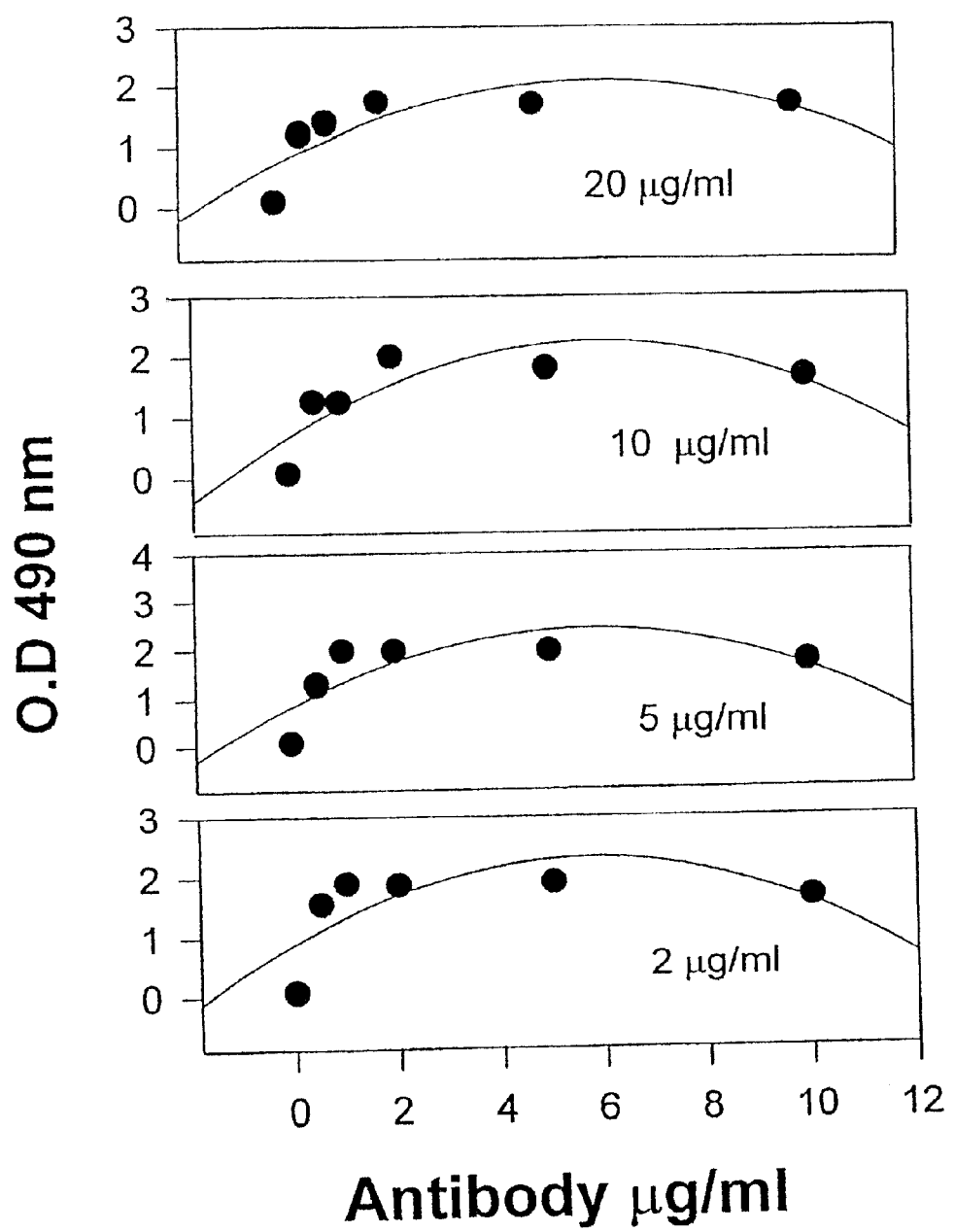
FIG. 7 shows determination of concentrations of streptavidin and 3C/G4-biotin conjugate for an indirect coat antibody.

FIG. 7 shows a determination of concentrations of streptoavidin and 3C/G4-biotin conjugate for indirect coating antibody at concentrations ranging from 2 to 20 μg/ml. These data illustrate that it is possible for 2 μg/ml of streptoavidin and 5 μg/ml 3C/G4-biotin conjugate to produce maximum binding.

Table 3 provides composition information for various solutions used herein for coating microplates used in the ELISA according to the invention.

TABLE 3

Composition of Solutions Used in ELISA Preparation

| | |
|---|---|
| 0.1M Na$_2$HCO$_3$ | 8.4 g Na$_2$HCO$_3$; 8.8 g NaCl; 0.1 g NaS. Adjust pH to 8.0 with NaCO$_3$; add ddH$_2$O to 1 L |
| Washing Solution | 6.8 ml of 1M Na$_2$HPO$_4$; 3.2 ml of 1M NaH$_2$PO$_4$; 1 ml of Tween ™-20. Add ddH$_2$O to 1 L |
| Block Solution | 1 g of BSA powder Add 0.1M Na$_2$HCO$_3$ buffer to 100 ml |

Preparing HLA-G Standard. Purified HLA-G from human first trimester placenta tissue was used as standard of this assay system. The purification of HLA-G protein has been described in *Purification of HLA-G, a Laboratory Manual*, (Yie S. M., 1997).

Figure 8:
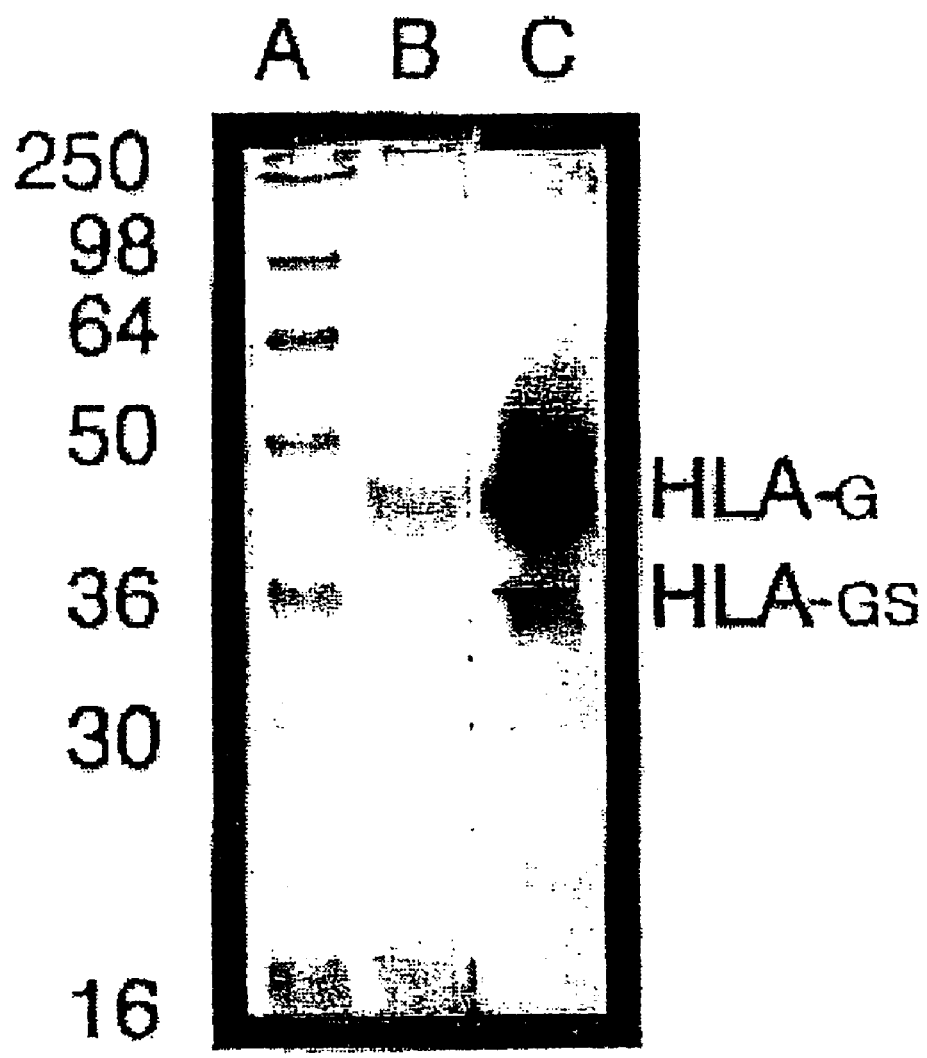
FIG. 8 shows purified HLA-G protein characterized by SDS-PAGE™ and Western blot.

FIG. 8 shows a purified placental HLA-G protein characterized by SDS-PAGE™ and Western blot. Purity of the protein was over 95%. Lane A shows the molecular weight maker; Lane B shows a fraction eluted from 4H84 mAb and βMM1 mAb affinity columns; and Lane C shows immunoblot of purified HLA-G protein using 4H84 mAb, illustrating locations of HLA-G and HLA-Gs.

Figure 9:
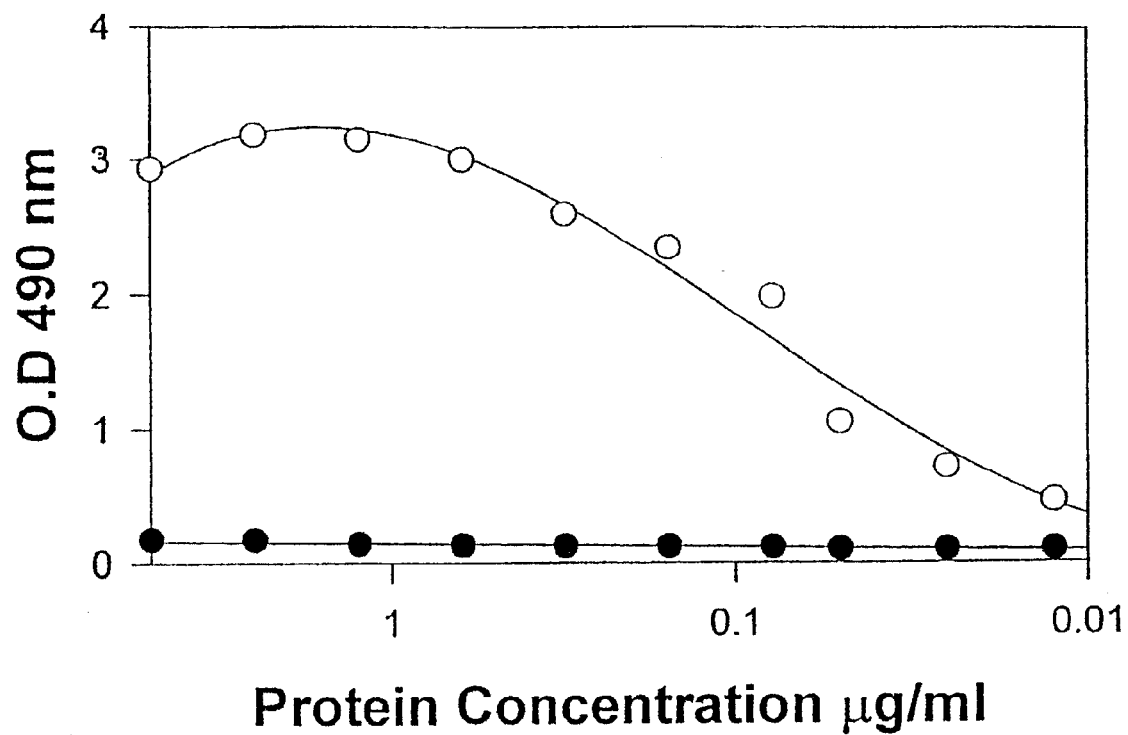
FIG. 9 shows purification of HLA-G protein, checked by ELISA. Various concentrations of purified HLA-G protein were first coated and then incubated with 3C/G4 antibody plus anti-mouse antibody (o) or with an anti-mouse antibody alone (●).

FIG. 9 shows a purification of HLA-G protein, as checked by ELISA. Various concentrations of purified HLA-G protein were first coated and then incubated with 3C/G4 antibody plus anti-mouse antibody as shown with open circles (○), or with anti-mouse antibody alone as shown with closed circles (●). These results illustrate that no antibody contamination was detected.

Preparation of ELISA. 50 μl per well of HLA-G standard from 0 to 0.5 μg/ml prepared in 0.01M PBS and 50 μl of serum were added to plate and incubated at 4° C. overnight. The plate was washed three times with the washing solution. 50 μl per well of 2C/C8-HRP conjugate (10 μg/ml) in 0.01M PBS was added and incubated at room temperature for 1 to 2 hours. The plate was washed three times with the washing solution.

o-phenylenedianine (OPD) solution (1.5 mg/ml) (Sigma™) was prepared in 0.1 M acetate buffer (pH=4.0). Hydrogen peroxide (4 μl of a 30% solution) was added to 10 ml OPD solution before adding 100 μl/well of substrate solution to wells. The plate was incubated at room temperature for 10 to 15 min. The reaction was stopped by adding 100 μl per well of 1N H$_2$SO$_4$. The plate was read at 490 nm in an ELISA reader.

Table 4 provides composition information for various solutions used in the preparation of the ELISA plate.

TABLE 4

Composition for Various Solutions

| | |
|---|---|
| 0.1M PBS/saline buffer pH = 7.2 | 6.8 ml of 1M Na$_2$HPO$_4$; 3.2 ml of 1M NaH$_2$PO$_4$; 8.8 g NaCl. Add ddH$_2$O to 1 L. |
| 0.1M Acetate buffer | 4.4 g sodium acetate. Adjust pH to 4.5 with acetic acid. Add ddH$_2$O to 500 ml |
| OPD solution | 15 mg OPD. Dissolved in |

TABLE 4-continued

Composition for Various Solutions

| | |
|---|---|
| | 10 ml acetate buffer. Add 0.4 μl/ml of H$_2$O$_2$ to the solution just before adding to plate. |

Performance Characteristics

Figure 10:
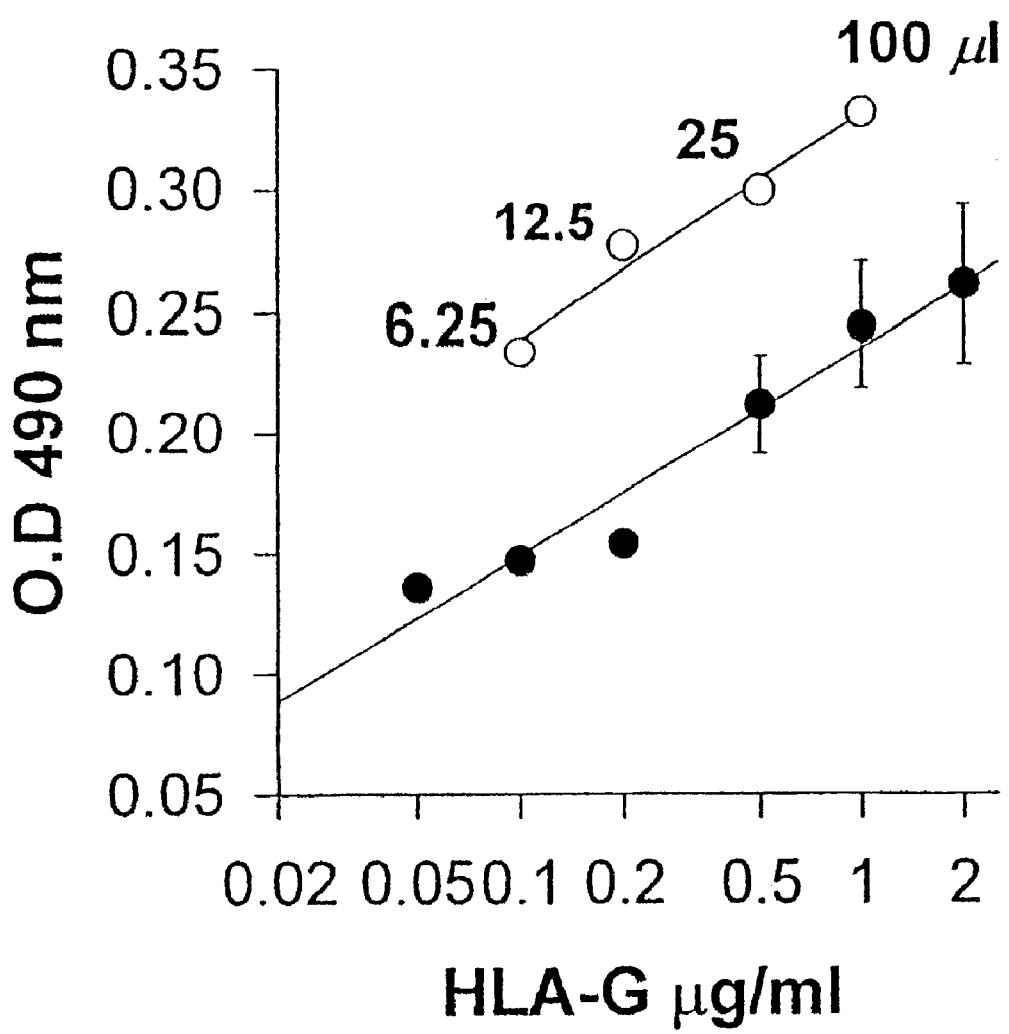
FIG. 10 shows a standard curve and a parallelism test of HLA-G in serum.

FIG. 10 illustrates a standard curve and parallelism test of HLA-G in serum. Serum values are shown with open circles (○), while the standard curve values are shown with closed circles (●). The serum dilution curve takes the form Y=0.121+0.106(log X), r=0.992. The standard curve takes the form Y=0.236+0.086(log X), r=0.975. These results show that the binding in serum was identical from HLA-G standard.

The sensitivity of the assay or lower limit of detection (LLD) was determined by assaying replicates of zero and the standard curve. The mean signal of zero plus 2 SD read in dose from the standard is the LLD≅10 ng/ml. This ELISA is specific for the measurement of natural HLA-G. It does not cross react with classical class I antigens, as shown by results herein (see Table 1). The within and between assay CV (variation) were 9.8% and 11%, respectively.

Table 5 shows mean assay recovery. The accuracy of the assay was estimated by a recovery test of spiked purified HLA-G protein.

TABLE 5

Assay Recovery

| HLA-G added μg/ml | Measured Value μg/ml | Calculated Value μg/ml | Recovery % |
|---|---|---|---|
| 0 | 1.011 | 1.011 | — |
| 0.2 | 1.222 | 1.211 | 100.9 |
| 0.4 | 1.366 | 1.411 | 94.6 |
| 0.8 | 1.949 | 1.811 | 107.6 |

Miniaturization of the HLA-G Assay. Pregnancy rates from transferred embryos having positive HLA-G secretion were significantly higher than those with undetectable HLA-G. Thus, to ascertain whether an embryo to be transferred has an increased likelihood of leading to pregnancy, a HLA-G detection assay can be conducted. However, the time required for detection is extremely limited, for example during an IVF procedure, and an accurate measurement taken within a clinical setting is desirable. A miniaturized HLA-G detection method can be used in a clinical setting so as to provide a rapid quantitative measurement of HLA-G in the medium in which an embryo is incubated, without requiring that a sample be sent off for laboratory analysis. Such a rapid detection assay advantageously involves either a visually distinguishable end-point (ie—colorimetric) or may involve a reader which is either hand-held, or bench-top sized, using an enzymatic, fluorometric or colorimetric end-point.

A miniaturized assay according to the invention may involve any device or method for analyzing a biological sample, such as is known in the art. The assay may be present on a support, such as on a strip or a chip, formed of plastic, cellulose, or any other acceptable material. By conducting the assay according to the invention in a miniaturized fashion, there is a reduced requirement for larger pieces of laboratory equipment. Further, there is less waste, as individual samples can be assessed with small amounts of biological fluids ranging from levels as low as 2 to 50 μl. A miniaturized assay, requiring a small sample volume allows detection even when sample size is severely reduced.

A miniaturized assay may have any acceptable form of detectable end-point so that the quantity of HLA-G present may be readily determined.

Exemplary embodiments of the invention are discussed below, which are not to be considered limiting to the invention.

EXAMPLE 1

ELISA for Detection of HLA-G in Serum

Serum samples were collected from non-pregnant healthy women, pregnant women at first trimester and term, patients after miscarriage, pre-eclampsia, and inter uterine growth retardation (IUGR). An ELISA assay according to the invention was conducted, using 96-well plates prepared with immobilized 3C/G4 antibody, in which samples were incubated. HRP-labeled 2C/C8 binding was detected with OPD.

Table 6 illustrates mean values of serum HLA-G, as determined according to the invention. These data illustrate that the inventive assay is effective in the detection of serum HLA-G.

TABLE 6

Serum HLA-G Values

| Group | N | Mean ± SE ($\mu$g/ml) |
| --- | --- | --- |
| Normal women | 9 | 0.117 ± 0.008 |
| Pregnant (first trimester) | 9 | 0.898 ± 0.024 |
| Pregnant (term) | 14 | 0.896 ± 0.039 |
| Miscarriage | 9 | 0.355 ± 0.010 |
| Pre-eclampsia | 14 | 0.242 ± 0.021 |
| IUGR | 11 | 0.121 ± 0.005 |

EXAMPLE 2

Serum and Placental HLA-G is Decreased in Women with Pre-eclampsia

HLA-G levels in serum and placenta tissues from women with pre-eclampsia at term were compared with levels in normal pregnant women. HLA-G levels were determined by using an ELISA according to the invention in 20 subjects with pre-eclampsia and 14 control pregnant women. Both serum and placental HLA-G levels were significantly decreased in the pre-eclampsia group (median 0.026 $\mu$g/ml in serum and median 0.026 $\mu$g/mg protein in placenta), in comparison with normal pregnant women (median 0.093 $\mu$g/ml in serum and median 0.088 $\mu$g/mg protein in placenta, p=0.0112 and p=0.0406, respectively). There was a significant correlation between serum and placental HLA-G levels (r=0.603, p=0.002). The impaired expression of HLA-G suggested that there was an alternation of the maternal-fetal immune relationship in pre-eclampsia and decreased HLA-G plays a role in etiology of the disorder.

Pre-eclampsia is a disease that affects of approximately 7% of pregnant women. It remains the most leading cause of maternal death in many western countries. The illness is ultimately cured when the uterus is emptied of placenta tissues, implying a direct role of the placenta in it's pathophysiology. Despite extensive study, its underlying etiology still remains an enigma.

Many hypotheses have been proposed to elucidate the mechanisms of the development of pre-eclampsia. One implies that pre-eclampsia involves some type of incompatibility between mother's immune system and the semi-allogeneic fetal allograft. Some evidence has emerged to support the idea that the maternal immune system is activated in pre-eclamptic patients (Hara et al., *Am. J. Reprod. Immunol,* 1995: 34:44–51). Expression of HLA-G protein, semi-quantitatively determined by immunohistochemistry and HLA-G mRNA northern blot analysis, is decreased in pre-eclamptic cytotrophoblasts compared with controls.

HLA-G is a non-classical class I antigen that is only expressed on extravillous cytophoblast of placenta and is almost monomorphic. It is also secreted as a truncated form of protein. HLA-G may play a critical role in maternal immune tolerance to the fetus. A line of experimental evidences demonstrated that HLA-G may protect fetal-placental unit from natural killer cell lysis, cytotoxic T cell activity and modification of the type of maternal immune response. If pre-eclampsia is due to deficient maternal immune accommodation to the fetus, alternation of expression of HLA-G on pre-eclamptic placenta should be associated with etiology of the disease. Therefore, it is important to determine expression of HLA-G in pre-eclampsia by a quantitative method. A specific and sensitive sandwich ELISA was recently developed in our laboratory. By using this technique, HLA-G levels were measured in both serum and placenta tissue lysates from pre-eclamptic patients to determine whether there is a significant alternation of HLA-G levels in both circulation and placenta in pre-eclamptic patients compared with normal pregnant women.

Materials and Methods. Twenty pre-eclamptic patients and 14 normal pregnant women were involved in this study. All the subjects were seen in the labor and delivery suite of the Women's College Hospital (WCH), University of Toronto, Toronto, Canada from 1995 to 1997. This study was approved by the ethics committee of WHC. Pre-eclampsia was diagnosed according to the criteria of Chesley (*Obstet Gynecol:* 1985:65:423–425). None of these patients had a history of intra uterine infections, pre-term labor or premature rupture of membrane. Obstetrical summaries of the women with pre-eclampsia are shown in Table 7.

TABLE 7

Clinical Characteristics of Pre-eclamptic Patients

| Criteria | Pre-eclampsia |
| --- | --- |
| Age (yrs) | 25–40 |
| Parity (times) | 0 |
| Blood Pressure (mmHg) | 140–210/90–120 |
| Proteinuria (dipstick) | 2+–4+ |
| Gestation Age (week) | 29–40 |

Placenta tissues and serum samples were collected as follows. Blood taken from patients and normal controls during labor was collected in serum separation Vacutainer™ tubes (Becton Dickinson, N.J., USA). Serum was collected after centrifugation for 10 minutes at 600 g, aliquoted and stored at −70° C. Placental tissues from patients and normal controls were obtained soon after the delivery and a portion from the maternal surface was taken and stored in pieces at −70° C. until assay. Approximately 1 g of the placental tissue was homogenized and lysed in Tris-HCl lysate buffer containing 0.5% NP-40, 2.5 mM EDTA, and 200 mM phenylmethyl sulfonylfluoride (PMSF).

HLA-G protein was purified from first trimester placenta tissue, as described in part by Deniz G et al., J Immunol 1994: 152:4255–4261. Briefly, first trimester placentas were collected from patients who underwent elective terminations at the Women's College Hospital, Toronto, Canada and stored at −80° C. until used. Placenta tissue was homogenized in 50 mM Tris-HCl/0.15 M NaCl (Tris/NaCl)(pH 7.4) with a Brinkmann polytron homogenizer at 4° C. The homogenized tissues were washed three times with 0.05 M Tris-HCl/saline pH=7.4, and was resuspended in 10 times the pellet volume of lysate buffer containing 50 mM Tris-HCl/0.15 M NaCl, 0.5% Nonidet P-40 (NP-40), 2.5 mM ethylenediaminetetraacetic acid and 200 mM phenyl-methyl sulphonyl fluoride (PMSF) (Sigma). The suspension was mixed gently on a rocker at 4° C. overnight. The suspension was centrifuged at 39 000 g for 30 minutes at 4° C. and the supernatant lysate was collected. The lysate was obtained by centrifugation at 39,000 g for 30 minutes at 4° C. The placental lysate was first passed over a Sepharose™ precolumn to eliminate non-specific binding, and then applied to the following affinity column. HLA-G proteins were then isolated by sequential 4H84 mAb (against HLA-G) and βMM1 mAb (against β2-microglobumin) affinity columns.

After washing with 100 column volumes of 0.01 M phosphate-buffered saline (PBS), pH 7.2, bound HLA-G was eluted with 0.1 M glycine-HCl buffer, pH 3.0. Fractions were immediately neutralized with 1 M Tris, pH 8.0. Using a Bio-Rad protein assay kit (BioRad, Hercules, Calif.), fractions with high protein concentrations were pooled. For additional purity, the pool was applied to the anti-2m antibody, BMM 1, affinity column and HLA-G was eluted and neutralized as above. Purification and characterization of isolated HLA were analyzed with Western blot (McMaster et al, *J Immunol.* 1998:160:5922–5928) with the 4H84 mAb and Coomasie blue staining of the gel (Laemmli, Nature 1970: 227:680–685).

Immunoblotting involved purification of HLA-G and HLA-B7 proteins (1 g/lane) were resolved in 10% sodium dodecyl sulphate-polyacrylamide gel electrophoresis (SDS-PAGE) gels and electroblotted onto nitrocellulose membranes (Schleicher and Schuell, Keene, N.H.) (Towbin et al. (1979) *Proc Natl Acad Sci USA* 1979; 76:4350). Membranes were blocked in PBS containing 0.05% Tween-20 (Sigma, St. Louis, Mo.) and 5% Carnation™ non-fat dry milk (T-blotto) overnight at 4° C., and then incubated with mAb 4H84, HC10 (hybridoma supernatant diluted 1:1 in T-blotto), or normal mouse serum (diluted 1:100 in T-blotto), for 1 hour at room temperature. Membranes were washed three times (10 minutes/wash) with PBS-Tween, and incubated with horseradish peroxidase-conjugated goat anti-mouse immunoglobulin G (IgG-HRP; Amersham Life Science, Canada), diluted 1:2000 in PBS-Tween, for 1 hour at room temperature. Membranes were washed three times for 10 minutes each time and processed for chemiluminescence according to the manufacturer's instructions (ECL; Amersham Life Science) and exposed to autoradiography film (Kodak, Canada).

Two monoclonal antibodies against HLA-G protein were used for development of the ELISA used herein. The first was the mAb 4H84 which was a gift of S. Fisher and M. McMaster (University of California, San Francisco). 4H84 is prepared as disclosed in Canadian Patent Application 2,213,620 (Fisher et a.), filed Mar. 21, 1996. The mAb was generated by using a synthetic peptide corresponding to amino acids 61–83 of α1 domain of HLA-G (McMaster et al. J Immunol 1998: 60:5922–5928). The second, mAb 3C/G4, was produced by using purified HLA-G protein to immunize BALB/c mice (Charles River), as described herein. Three week old female mice were given i.p. injections of 100 μg purified protein/animal and were boosted after 2 repeat injections. Mice were killed three days later and splenocytes were fused with SP2/0 myeloma cells according to standard methods, after which cultures were selected in hypoxanthine-ampinopterin-thymidine medium and cloned by the limiting dilution method (Harlow E, Lane D: Monoclonal antibodies, *In: Antibodies: a Laboratory Manual,* edited by Harrow E and Lane D, Cold Spring Harbor Laboratory, Cold Spring Harbor, N.Y., pp 139–243, 1988).

Hybridomas were screened for reactivity against the purified HLA-G protein by Ab-capture ELISA. Lines that produced anti-HLA-G antibodies were further screened for their ability to react with the HLA-G heavy chain in cytotrophoblast and JEG-3 cell lysates by western blot and immunocytochemistry. Pooled white blood cell lysates were used to select lines that do not react with classical class I antigens. Comparison of antibody binding sites were examined by using antibody competition assay. 3C/G4 mAb was chosen because the mAb had the same specificity as 4H84 mAb, but it binds to a different epitope on HLA-G protein than 4H84 mAb. The class of the Ab was Ig A that was determined using an ImmunoType Kit (Amersham, Buckinghamshire, England).

The inventive ELISA was used for HLA-G analysis in serum and placenta lysates. The ELISA w as developed based on the principles described by Micallef et al. (Micallef J, Ahsan R: Immunoassay development, In: *Immunoassay: Laboratory Analysis and Clinical Applications,* Eds by Gosling J P and Basso L V, pp51–68, Butterworth-Heinemann, London, 1994). Each well of a 96-well immunoplate (Corning, N.Y. USA) was filled with 0.1 ml of 4H84 mAb (10 μg/ml) and kept at 4° C. overnight. Each well was washed three times with a 0.01 M PBS washing solution containing 0.05% Tween-20 and blocked with 1% BSA for 4 hours at room temperature. Serum or placenta lysate samples were added to a final volume of 0.1 ml in each well and incubated at 4° C. overnight. Wells were washed three times with the washing solution and to each well 0.1 ml of biotinylated 3C/G4 at optimum dilution was added. Plates were incubated for 2 hours at room temperature. All the wells were washed three times before adding 0.1 ml/well of 1:2000 dilution of streptavidin-HRP (Sigma Chemical Co., Louis, Md., USA) in 0.01M PBS containing 1% BSA and incubated for 1 hour at room temperature. Wells were washed three times before adding o-phenylenediamine substrate solution (1.5 mg/ml in 0.1 M acetic buffer, pH=4.5). After 10–15 minutes incubation at room temperature the reactions were then stopped by the addition of 0.1 ml of 0.1N $H_2SO_4$ to each well and plate was read at 490 run on an automated ELISA plate reader (Molecular Devices, USA). Curve fitting and dose interpolation were performed by software associated with the reader. Total protein concentrations of placenta lysates were determined by the Bio-Rad™ protein assay kit (Bio-Rad, USA). For statistical analysis, differences of HLA-G levels between normal pregnancy and pre-eclampsia were assessed for statistical significance using Mann-Whitney rank sum test. Least squares linear regression was used to correlate HLA-G protein levels in serum and placenta lysates.

Results. ELISA validation was conducted. The immunoaffinity purified HLA-G protein was used as standard in ELISA.

As illustrated in FIG. 8, the purity and characterization of purified HLA-G protein, as analyzed by SDS-PAGE and immunoblot, conducted as described above. The blot indicates that there are membrane bound and secreted HLA-G proteins. These data illustrate that the purification of standard was estimated more than 95%. The purified protein contained both the surface (38–39 Kd) and secreted forms (34–35 Kd) of HLA-G. No classical class I molecules could be detected at molecular weights in the 43 to 45 Kd range.

Figure 11:
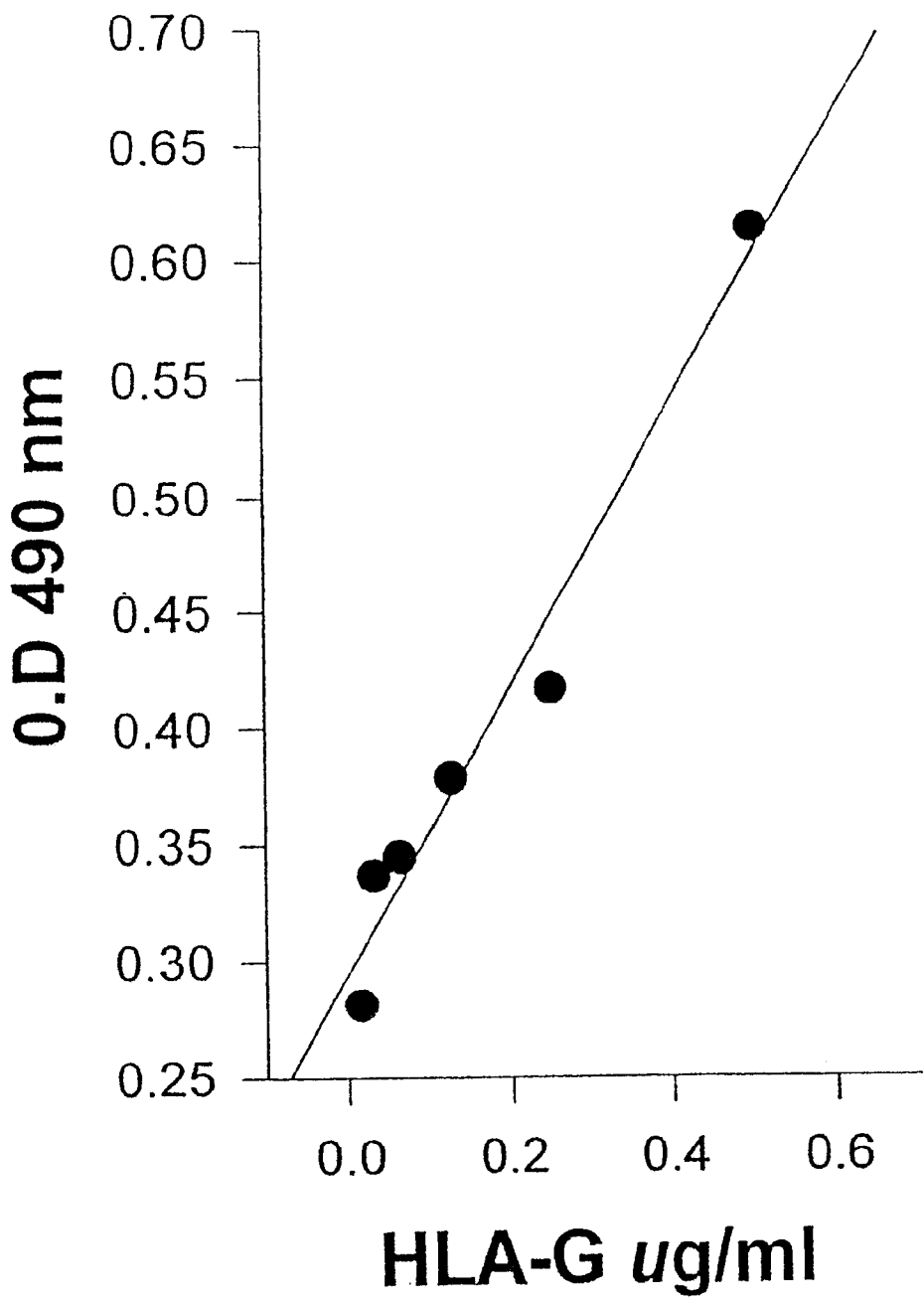
FIG. 11 illustrates a typical standard curve determined using the HLA-G ELISA according to the invention.

FIG. 11 shows a typical standard curve by HLA-G ELISA. This standard curve for the assay demonstrates a linear association between protein concentration and OD at 490 mn. The assay limit was less than 10 ng/ml. Variations of within and between assays were monitored using a placenta lysate pool of first trimester placenta tissues and the coefficients of variations obtained was less than 10%.

The overall recovery of purified HLA-G spiked into serum and placenta lysate was 101±6.5%, based on the data presented in Table 5 for added values ranging from 0 to 0.8 $\mu$g. Serially diluted serum and placenta lysate gave dose responses paralleled to that of the purified HLA-G protein further validating the inventive ELISA assay.

Serum concentrations of HLA-G protein in maternal serum samples were measured in 14 normal pregnant women. Values ranged from 0.016 to 4.396 with a median of 0.093 mg/ml. In contrast, HLA-G concentrations measured in serum from 20 patients with pre-eclampsia ranged from 0.009 to 0.590 with a mean of 0.026 mg/ml. The concentrations of serum HLA-G protein in pre-eclampsia were significantly lower than that in normal pregnant women, as shown in Table 8.

TABLE 8

Serum and Placental HLA-G Levels in Normal Pregnant Women and Women with Pre-Eclampsia at Term

|  | Normal Pregnant N = 14 | Pre-eclampsia N = 20 |
| --- | --- | --- |
| | Serum HLA-G $\mu$g/ml | |
| Median | 0.093* | 0.026* |
| 25% | 0.039 | 0.016 |
| 75% | 0.789 | 0.048 |
| | Placental HLA-G $\mu$g/mg protein | |
| Median | 0.088** | 0.026** |
| 25% | 0.019 | 0.014 |
| 75% | 0.124 | 0.056 |

*Mann-Whitney Rank Sum Test: T = 318, p = 0.0112
**Mann-Whitney Rank Sum Test: T = 304, p = 0.0406

Analysis of HLA-G protein in placental lysates from women with pre-eclampsia provided the following results. HLA-G protein concentrations in placenta lysate samples were normalized by their total protein concentrations representing as $\mu$g/mg protein. The HLA-G protein levels assayed in normal pregnant women ranged from 0.0065 to 0.2 with a median of 0.088 $\mu$g/mg protein. Patients with pre-eclampsia had concentrations ranging from 0.001 to 0.106 with a mean of 0.026 $\mu$g/mg protein. Consistent with the results in serum, placental HLA-G levels in normal pregnant women were significantly higher than those of pre-eclampsia patients.

Figure 12:
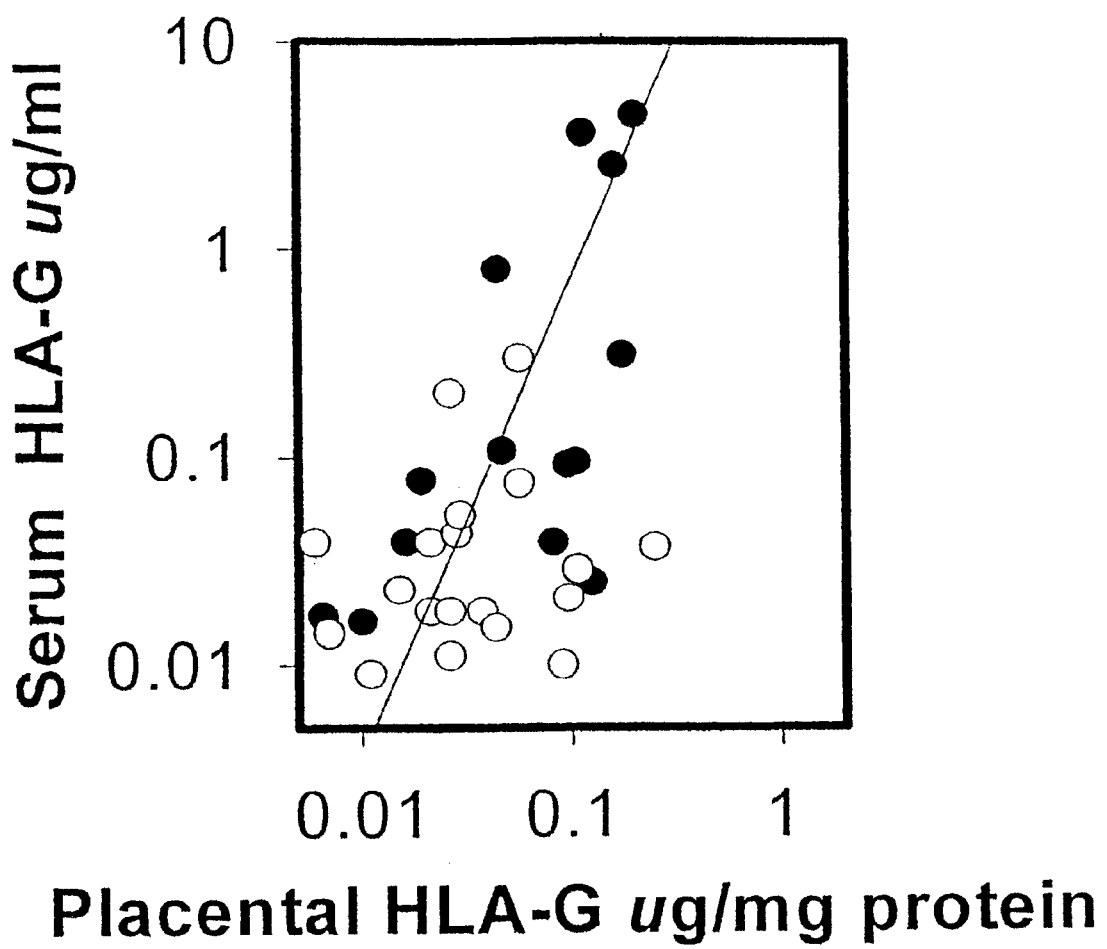
FIG. 12 shows a correlation between HLA-G protein concentrations in placenta and serum at term. HLA-G concentrations in normal pregnant women at term represented by the closed circles (●) and the pre-eclampsia by open circles (o).

FIG. 12 illustrates the correlation of HLA-G protein concentrations in placenta and serum at term. HLA-G concentrations in normal pregnant women at term are represented by the closed circles (●), and the pre-eclampsia by open circles (○). The data were analyzed by linear regression analysis (r=0.603, p=0.0002). These results show that there was a significant correlation between serum HLA-G concentrations and HLA-G levels in placenta lysates from the same patients (r=0.603, p=0.0002).

Discussion. According to the invention, two monoclonal antibodies to HLA-G were used that bind to different epitopes on the molecule to develop a highly sensitive and specific ELISA for measurement of this molecule's concentration.

The invention demonstrates for the first time that the quantity of HLA-G protein in pre-eclamptic placental tissue is significantly decreased as compared to normal pregnant placentas. These results confirm the findings by Hara et al., who used immunohistochemistry (Am. J. Reprod. Immunol 1996: 36:349–35), and Lim et al., (Am. J. Pathol 1997;151: 1809–1818), who used Northern blot analysis to show decrease HLA-G mRNA levels in isolated cytotrophoblast cells from pre-eclamptic placentas. Using ribonuclease protection assay, Globern et al. (Am. J. Obstet. Gynecol 1994:170: 1244–1250) reported that the level of HLA-G mRNA in pre-eclampsia placenta was reduced.

Figure 13:
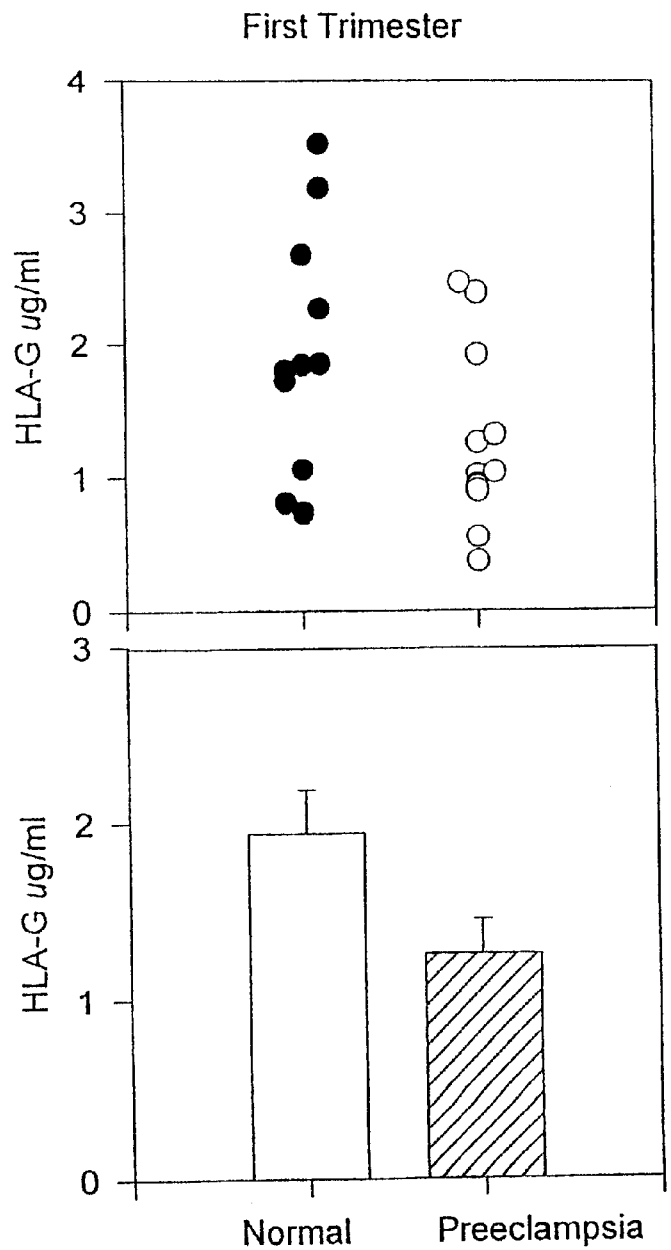
FIG. 13 shows serum HLA-G levels during the first trimester of pregnancy in normal women (●) and in pre-eclamptic women (o).

It is well established that extravillous cytotrophoblasts secrete a truncated form of HLA-G, but there are no reports determining HLA-G concentrations in the serum of pregnant women. The invention demonstrates the presence of HLA-G in serum obtained from normal pregnant women and women with pre-eclampsia by using our HLA-G specific ELISA. Serum HLA-G concentrations in women with pre-eclampsia were significantly lower than that in normal pregnant women. In addition, there was a significant correlation between serum HLA-G concentrations and placenta lysate levels, (as shown in FIG. 13).

Although HLA-G mRNA has been detected in other adult and fetal tissues by RT-PCR analysis (Crisa et al., J Exp. Med 1997: 186: 289–298), protein has not been detected in these tissues. Therefore, the placenta is the likely source of the majority of, if not all of the HLA-G detected in serum. The restricted expression and minimally monomorphic nature of HLA-G have resulted in many to hypothesize that HLA-G could serve as "universally acceptable identity card" to allow trophoblast cells to evade rejection by the maternal immune system. How HLA-G might function in this capacity is becoming more unclear. It has previously been demonstrated that HLA-G may prevent fetus-placenta unit from NK cell lysis. However, the instant inventors have demonstrated that HLA-G may inhibit the generation of cytotoxic cell activity (see Kupasi et al., Immunology 2000:101:1–14).

It is unknown what HLA-G may play, if any, in the pathophysiology of pre-eclampsia. Pre-eclampsia has been designed as a two stage disease; the initial stage involves poor placentation and the second stage is associated with placental ischemia. Clearly, immune mechanisms may have a primary role to play in the first stage of the pathogenesis of pre-eclampsia. In this stage, the impaired expression of HLA-G may not prevent the fetus-placenta unit from maternal immune rejection and subsequent fetal loss. With a milder degree of impairment, the pregnancy could continue with later evolution to syndrome from chronic immune attack resulting in placental ischemia. Some evidence suggests that cytokines such as tumor necrosis factor (TNF-$\alpha$) and interleukin (IL)-2 are increased in plasma and decidua from pre-eclamptic patients and serum IL-4 levels were decreased in pre-eclampsia. T cells that produce TNF-$\alpha$, IL-2 and IFN-$\gamma$ have been designated as Th1-type cells while T cells that secrete IL-3, IL-4, IL-10, IL-13 and TGF-$\beta$2 are Th2-type cells. Evidence would suggest that a Th1-type response is detrimental whereas a Th2-type response is beneficial for pregnancy (Clark, *Am. J Reprod. Immunol*, 1997: 38:75–78).

HLA-G in high concentrations of HLA-G result in a Th1-type response, whereas low concentrations of HLA-G result in a Th1-type response. Thus, the decrease of HLA-G expression in pre-eclampsia may be associated with alternations in the maternal immune response pattern corresponding to a Th1 type.

In conclusion, the invention demonstrates that HLA-G levels in both serum and placenta were decreased in women with pre-eclampsia at term as compared to normal pregnancy. Serum levels are significantly correlated with placental levels in these two groups. Alternations in HLA-G expression may play a role in pathophysiology of pre-eclampsia.

EXAMPLE 3

Differences in Serum Human Leukocyte Antigen-G (HLA-G) in Normal and Pre-Eclamptic Women at During Different Trimesters of Pregnancy Serum samples were collected from normal pregnant women or from pre-eclamptic women at first trimester, second trimester and third trimester (N=12). An ELISA assay according to the invention was conducted, using 96-well plates prepared with immobilized 3C/G4 antibody, in which samples were incubated. HRP-labeled 2C/C8 binding was detected with OPD.

FIG. 13 illustrates the data points and median values for HLA-G levels in serum taken from women in the first trimester of their pregnancy either during a normal pregnancy, shown in closed circles (●), or during pre-eclampsia, shown by open circles (○).

Figure 14:
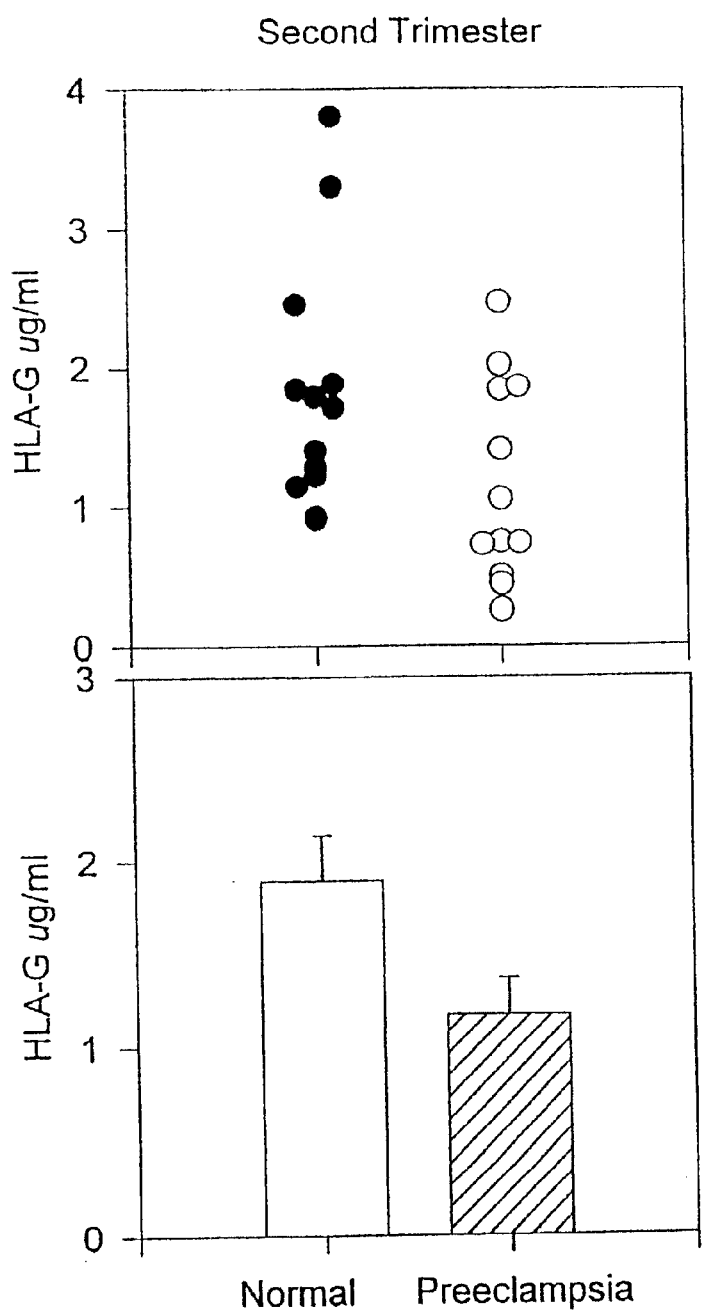
FIG. 14 illustrates serum HLA-G levels during the second trimester of pregnancy in normal women (●) and in pre-eclamptic women (o).

FIG. 14 illustrates the data points and median values for HLA-G levels in serum taken from women in the second trimester of their pregnancy either during a normal pregnancy, shown in closed circles (●), or during pre-eclampsia, shown by open circles (○).

Figure 15:
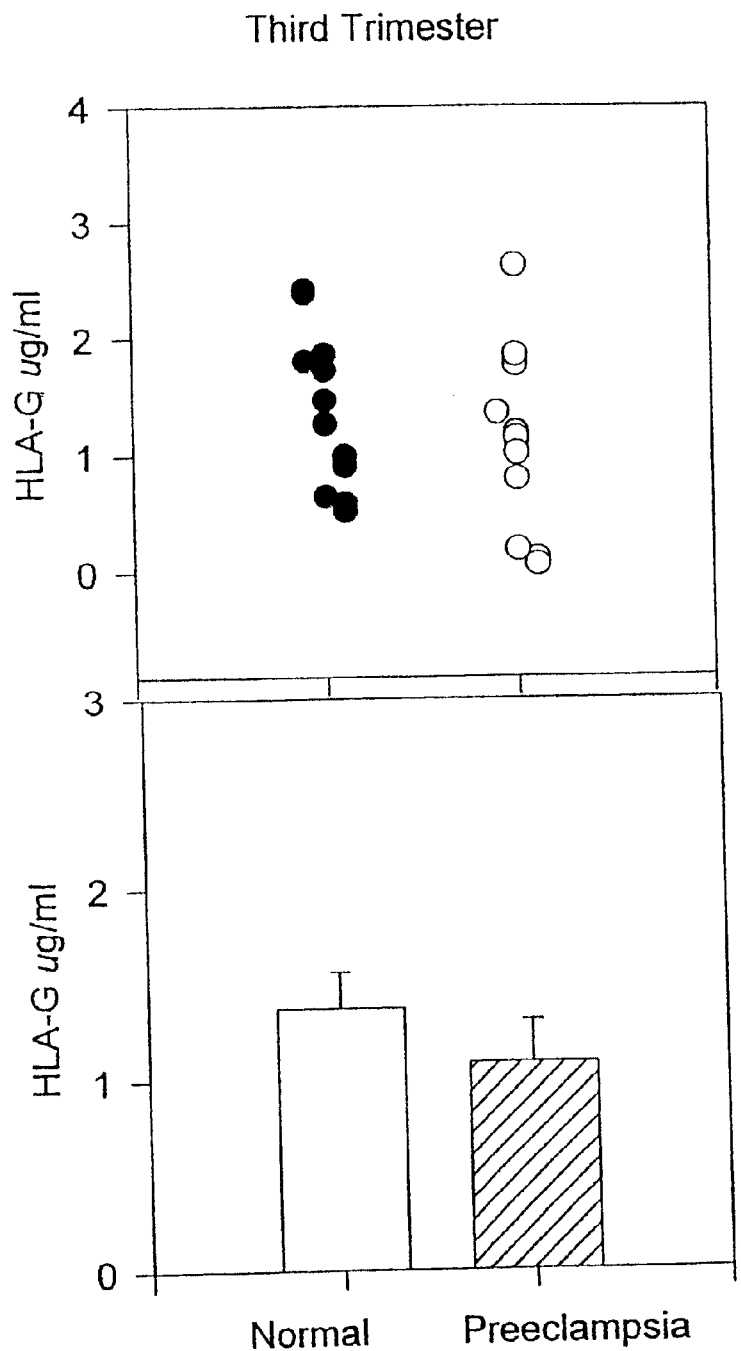
FIG. 15 shows serum HLA-G levels during the third trimester of pregnancy in normal women (●) and in pre-eclamptic women (o).

FIG. 15 illustrates the data points and median values for HLA-G levels in serum taken from women in the third trimester of their pregnancy either during a normal pregnancy, shown in closed circles (●), or during pre-eclampsia, shown by open circles (○).

These data illustrate that the inventive assay is effective in the detection of serum HLA-G, and also that early stages in pregnancy (first and second trimester) are best for detection of pre-eclampsia based on serum HLA-G, as this is when differences between normals and pre-eclamptic subjects are most pronounced.

EXAMPLE 4

Progesterone Increases HLA-G Expression in vitro

HLA-G is expressed on placental tissues at the maternal-fetal interface. This restricted pattern of expression suggests that HLA-G may play a crucial role in maternal immune tolerance to the fetus. It has been reported that HLA-G expression is developmentally regulated and changes with stage of gestation. There are conflicting reports that the cytokine gamma IFN has an effect on HLA-G expression in vitro. Since, some studies suggest that progesterone is important in suppressing the maternal immunological response to the fetus, it was hypothesized that this steroid hormone may play a role in regulating HLA-G expression. The present study was performed to explore potential effects of progesterone on HLA-G expression in cytotrophoblasts and in the JEG-3 choriocarcinoma cell line in vitro.

Methods. Purified cytotrophoblasts were prepared from first trimester placental tissue by standard techniques. JEG-3 choriocarcinoma cells were cultured in RPMI-1640 medium containing 10% FCS for three days. The cells were then treated with various doses of progesterone for 24 hours. Cell lysates and conditioned media were prepared for ELISA and total RNA was extracted for PCR. The ELISA was conducted according to the invention, using the 3C/G4 and 2C/C8 anti-HLA-G monoclonal antibodies. HLA-G protein, purified by immunoaffinity columns from first trimester placental tissue, was used as standard. The sensitivity of the ELISA was 20 ng/ml and assay variation was less than 10%. Quantitative RT-PCR was performed by using specific primers for HLA-G. Results were assessed for statistical significance using one-way analysis of variance.

Results. HLA-G protein in placenta cell culture was significantly increased by progesterone at doses of 100 ng and 1000 ng/ml. Progesterone also had a stimulating effect on HLA-G concentration in both JEG-3 cell lysate and conditioned medium with a significant increase at doses from 10 ng/ml. The results of RT-PCR indicated an increase of HLA-G mRNA levels after progesterone treatment in both JEG-3 and cytotrophoblast cells. Cells treated with a 1000 ng/ml concentration of progesterone showed significantly higher HLA-G mRNA levels than that measured after exposure to 10 and 100 ng/ml concentrations.

Conclusion. These data suggest that progesterone regulates HLA-G expression in vitro. Progesterone may thus be involved in regulation of placental HLA-G expression. Since HLA-G may play an important role in maternal immune tolerance to the fetus, it is possible that one mechanism of immunosupression by progesterone during pregnancy is by a means of modulating HLA-G expression. Further, this study indicates that the method of HLA-G detection according to the invention is effective for measuring HLA-G from in vitro cell lysates, including carcinoma cell lines.

EXAMPLE 5

Secretion of Human Leukocyte Antigen-G (HLA-G) by Human Embryos is Associated with a Higher IVF Pregnancy Rate It is shown herein that transfer of human embryos that secrete HLA-G results in a higher IVF pregnancy rate than transfer of embryos lacking HLA-G secretion. The combination of HLA-G detection and a higher embryo cleavage rate is an excellent predictor of IVF outcome.

Human leukocyte antigen G (HLA-G) is a non-classical class I antigen that may play an important role in maternal-fetal immune tolerance (Rouas-Freiss et al. Proc. Nat. Acad. Sci. USA, 1997; 94:11520–5). In pregnancy, HLA-G is expressed on the placental cytotrophoblast cells at the maternal-fetal interface (Le Bouteiller et al. Immunol Rev. 1999; 167:233–44.). HLA-G protein is detectable by immunocytochemistry (ICC) in some human pre-implantation embryos (Jurisicova et al. Proc. Nat. Acad. Sci. USA. 1996; 93:161–5).

In placenta and some chroriocarcinoma cell lines, alternative splicing of the HLA-G gene results in six different transcriptional isoforms, four of which encode potential membrane-bound products, while two others encode soluble proteins. In normal tissues one surface bound (G1) and one soluble form have been shown to be translated. The G1 form is most analogous to the classical class I cell surface molecules. In some tumors and tumor cell lines the other forms may exist (Paul et al. Proc. Natl. Acad. Sci. USA. 1998, 95:4510–5.). Soluble HLA-G (sHLA-G) has been detected in amniotic fluid, and in maternal plasma and in cell culture supernatants from trophoblast-derived cell lines (Rebmann et al. Tissue Antigens 1999:53: 14–22; Fournel et al., Am J Reprod Imnunol 1999: 42:22–29). Sibling embryos from patients that became pregnant with in vitro fertilization (IVF) were significantly more likely to express HLA-G on their cell surface than embryos from patients that did not conceive (Jurisicova et al., Fertil Steril 1996; 65:997–1002). Therefore, this study was designed to determine whether human embryos secrete HLA-G and to analyze any associations between sHLA-G detection and embryo development or IVF pregnancy outcome. One objective of this investigation was to ascertain whether human embryos secrete soluble human leukocyte antigen G (sHLA-G) and whether the secretion of sHLA-G is associated with embryo development and IVF pregnancy outcome.

Design. Three hundred and eighty six embryo culture conditioned media samples were collected from 137 IVF cycles. HLA-G concentrations in the samples were assayed by a specific and sensitive ELISA. Potential associations between sHLA-G and pregnancy rate as well as other factors known to influence IVF outcomes were analyzed.

Patients and IVF. A total 137 of couples undergoing IVF at the Success Through Assistant Reproductive Technology (S.T.A.R.T) IVF laboratory in Toronto, Canada were involved in this study. Ovarian stimulation was carried out using a standard protocol as previously described (Gonen et al., Fertil Steril 1990: 53:282–7; Segal et al., Human Reprod 1992; 7:1210–3). From these patients, a total of 386 embryo cultured medium samples were collected. All of these were from embryos cultured in vitro for entire 72 hours. All samples were from cases where intracytoplasmic sperm injection (ICSI) was used for fertilization (Palermo et al., Lancet 1992; 340: 17). These embryos were in the same culture medium for the entire time 72 hours. Fertilization was confirmed by observation of two pro-nuclei. The number of embryos cultured per well ranged from 1 to 7 with an average of 2.90. The embryo quality was scored by grade and number of blastomeres according to the Veek classification system. Embryos with the highest grade and number of blastomeres were selected for transfer and the remaining viable embryos were cryopreserved. Successful pregnancy was defined as a live birth. Spontaneous abortion was defined as the presence of a sonographically detectable sac in the uterus. Chemical pregnancies were not included in the pregnant group.

Embryo Culture Conditioned Medium. Embryos were cultured in HTF medium containing 10% human serum albumin (GIBCO/BRL, Gaithersburg, Md., USA). Culture took place in 0.4 ml of medium under 500 $\mu$l of paraffin oil in a cell culture incubator (5.5% $CO_2$ at 37° C.). After three days the embryos were selected for transfer and approximately 200 $\mu$l of the culture medium from each well was collected and stored at −80° C. until assay. As a control, culture medium without embryos was included and frozen in the same manner.

Purification of HLA-G Protein. Native HLA-G protein from first trimester placental tissue as described herein. Briefly, the placenta tissues were homogenized with a Brinkmann polytron homogenizer at 4° C. The homogenized tissues were washed three times with 0.05 M Tris-HCl/saline pH=7.4 before solubilizing in 0.5% NP-40 in 0.05 M Tris-HCl/saline containing 2.5 mM EDTA and 200 mM PMSF at 4° C. overnight. The lysate was obtained by centrifugation at 39,000 g for 30 minutes at 4° C. HLA-G protein was then isolated by sequential 4H84 mAb (against HLA-G) and βMM1 mAb (against β2-microglobumin) affinity columns. Purity of isolated HLA-G protein was confirmed by Western blotting with the 4H84 mAb and Coomasie blue staining of the gel.

Monoclonal Antibodies. Two mAbs against HLA-G protein were used for development of our ELISA. The first was the mAb 4H84 which was a gift of S. Fisher and M. McMaster (University of California, San Francisco). This mAb was generated by using a synthetic peptide corresponding to amino acids 61–83 within the α1 domain of HLA-G (McMaster et al., J Immunol 1995; 154:3771–8).

The second monoclonal antibody 3C/G4, was produced according to the invention using purified HLA-G protein preparation to immunize BALB/c mice (Charles River). Three-week-old female mice were given i.p. injections of 100 $\mu$g purified protein/animal and were boosted with 2 repeat injections. The mice were sacrificed three days later and their splenocytes were fused with SP2/0 myeloma cells according to standard methods (Harlow E, Lane D: Monoclonal antibodies. In: Harrow E and Lane D, eds. Antibodies: a laboratory manual. NY: Cold Spring Harbor Laboratory, 1998:139–243). Cultures were selected in hypoxanthine-ampinopterin-thymidine medium and cloned by the limiting dilution method. Hybridomas were screened for reactivity against the purified HLA-G protein by Ab-capture ELISA according to standard methods. Cell lines that produced anti-HLA-G Abs were further screened for their ability to react with the HLA-G heavy chain in cytotrophoblast and JEG-3 choriocarcinoma cell lysates by western blot and immunocytochemistry. Pooled white blood cell lysates were used to select lines that do not react with classical class I antigens. Comparison of antibody binding sites was examined by using an antibody competition assay. 3C/G4 mAb was chosen for the ELISA because it has the same specificity for HLA-G as 4H84 mAb, but it binds to a different epitope on the HLA-G heavy chain, thereby having a different binding region.

Figure 16:
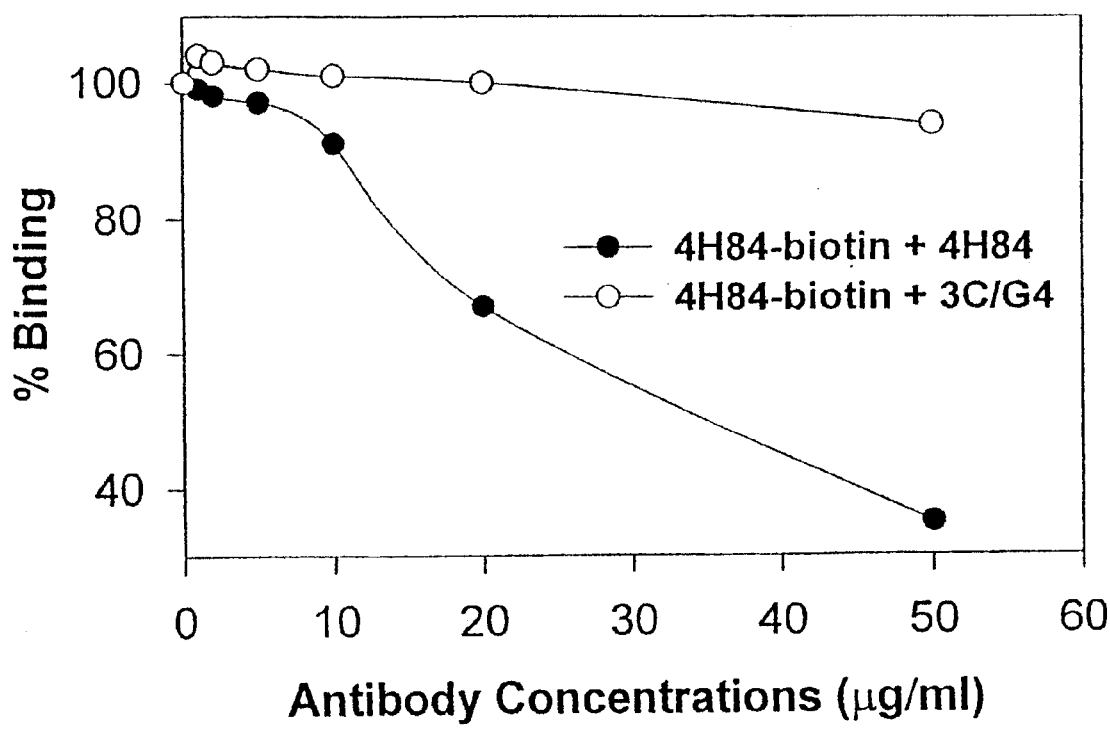
FIG. 16 illustrates an antibody competition assay to compare antibody binding sites of two HLA-G monoclonal antibodies, 4H84 (●) and 3C/G4 (o).

FIG. 16 illustrates an antibody competition assay to compare antibody binding sites of two monoclonal antibodies against HLA-G (4H84 and 3C/G4). In the assay, a fixed amount of biotin labeled purified 4H84 antibody was added together with various doses of unlabeled 4H84 antibody (control) or unlabeled 3C/G4 antibody to an ELISA plate coated with purified HLA-G protein. 3C/G4 binds to a different epitope on HLA-G than 4H84 since no binding competition between these two antibodies (open circles).

ELISA for HLA-G in Embryo Culture Medium. The ELISA was developed based on the principles described by Micallef et al (Micallef J, Ahsan R: Immunoassay development. In: Gosling J P and Basso L V, eds. Immunoassay: Laboratory Analysis and Clinical Applications. London: Butterworth-Heinemann, 1994:51–68). Each well of a 96-well immunoplate (Corning, N.Y., USA) was filled with 0.1 ml of 4H84 mAb (10 $\mu$g/ml) and kept at 4° C. overnight. Each well was washed three times with a 0.01 M PBS washing solution containing 0.05% Tween-20 and blocked with 1% BSA for 4 hours at room temperature. Duplicate embryo cultured medium samples were added to a final volume of 0.1 ml in each well and incubated at 4° C. overnight. Wells were washed three times with the washing solution and to each well 0.1 ml of biotinylated 3C/G4 at optimum dilution was added. The plate was incubated for 2 hours at room temperature. All the wells were washed three times before adding 0.1 ml/well of a 1:2000 dilution of streptavidin-HRP (Sigma Chemical Co., St. Louis, Md., USA) in 0.01M PBS containing 1% BSA, and then incubated for 1 hour at room temperature. Wells were then washed three times before adding 150 $\mu$l of TMP substrate solution (Sigma Chemical Co. St. Louis, Md., USA). After 10–15 minutes incubation at room temperature the reactions were then stopped by the addition of 50 µl of 1 M HCl to each well and plate was read at 450 nm on an automated ELISA plate reader (Molecular Devices, USA). Curve fitting and dose interpolation were performed using software associated with the reader.

Statistical Analysis. Embryo conditioned medium was scored as HLA-G positive or negative according to whether sHLA-G was detectable or not by Elisa. For the propose of these analyses, any cases where at least 1 embryo transferred came from a HLA-G positive well was scored as positive. Differences concerning patient's age, embryo grade, embryo cleavage rate, and number of embryos per culture well between the two groups were assessed for statistical significance by using the Student's t test or Mann-Whitney rank sum test depending upon whether the data had a normal distribution. sHLA-G concentration and embryo cleavage rate the in data was compared by using the Kruskal-Wallis one-way analysis of variance on rank. Chi-square analysis was used to compare pregnancy rates between various groups.

Results. 270 of 386 samples had detectable sHLA-G. Detection of sHLA-G secretion was independent of embryo grade and patient's age. The cleavage rate of embryos with detectable sHLA-G was significantly higher than those without sHLA-G (number of blastomerers 6.71±0.09 vs 5.86±0.22, p=0.0061). Live birth rates from transferred embryos with positive sHLA-G secretion were significantly higher than those with undetectable HLA-G (45% vs 16.2%, $\chi 2$=8.38, p=0.0038). Combining sHLA-G and cleavage rate were the best prediction of IVF success. Secreted HLA-G (sHLA-G) was detectable in 270 out of 386 embryo conditioned medium samples (69.9%) and concentrations ranged from 0.01 µg/ml to 1.89 µg/ml with a mean of 0.165 µg/ml. Age, embryo grade and number of embryos per culture well were compared between HLA-G detectable and undetectable groups.

Table 9 illustrates that there were no significant differences in these factors between the two groups. Samples were grouped into HLA-G negative and positive groups according to whether sHLA-G was detectable by the ELISA or not.

TABLE 9

Comparison of Patient's Age, Embryo Grade and Number of Embryos per Culture Well Between HLA-G Negative and Positive Groups

|  | Patient's Age (yr)** | Grade of embryos* | No. Embryos/well* |
|---|---|---|---|
| HLA-G (+), N = 116 | 35.0 ± 0.52 | 2.40 ± 0.08 | 2.80 ± 0.14 |
| HLA-G (+), N = 270 | 34.4 ± 0.29 | 2.41 ± 0.04 | 2.83 ± 0.08 |
| Significance | NS | NS | NS |

*Tested by Mann-Whitney rank sum test.
**Tested by Student's t test. All data are presented as mean ± SE.

Figure 17:
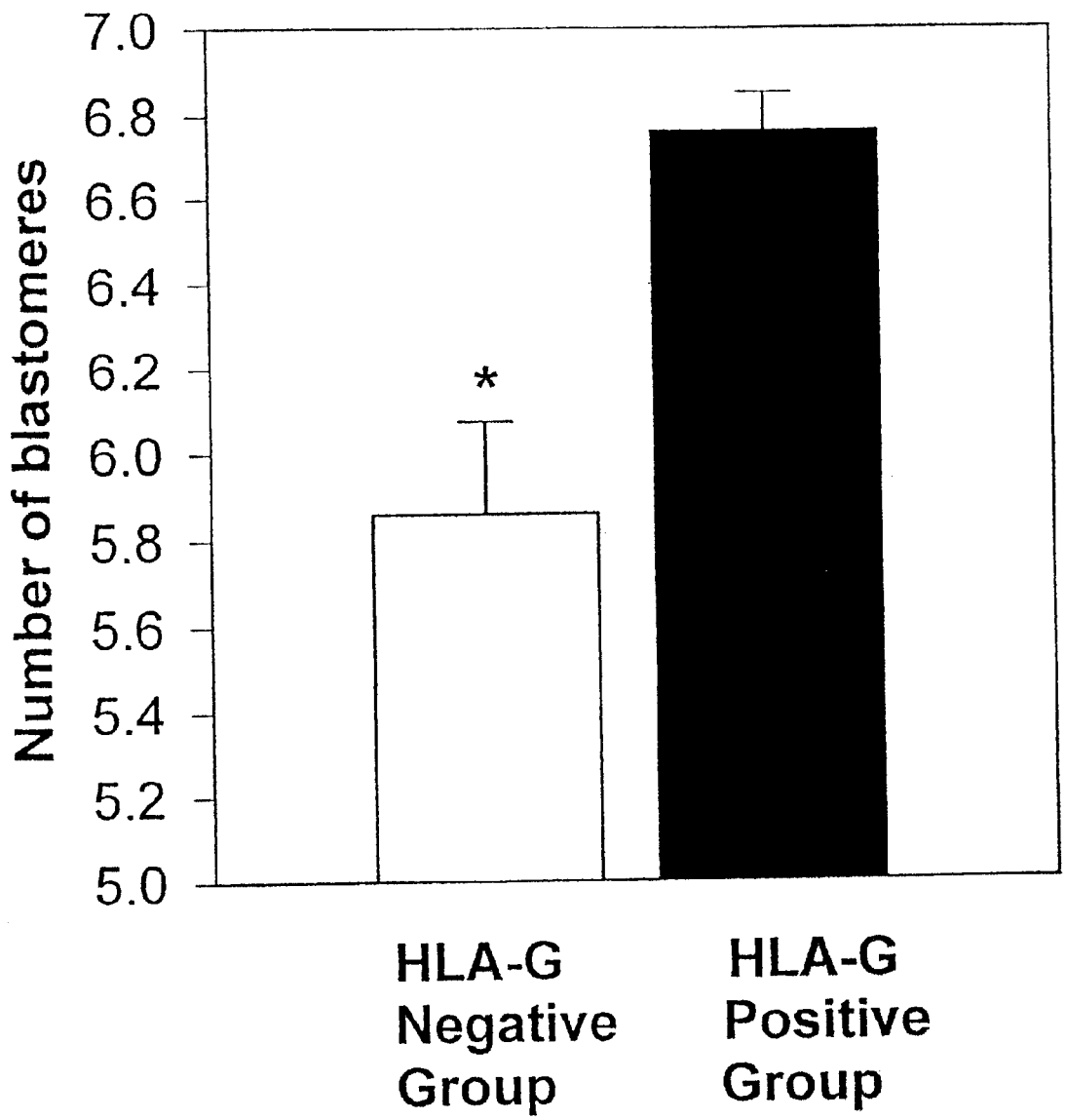
FIG. 17 shows a comparison of the number of blastomeres in samples testing negative versus those testing positive for HLA-G in medium.

FIG. 17 shows that a significant difference in embryo cleavage rate (number of blastomeres: 6.76±0.09 vs 5.86±0.22, p=0.0061) between the two groups was observed. The HLA-G positive group samples were further divided into four sub-groups according to average number of blastomeres per culture well (group 1:≦4, group 2:>4=6, group 3:>6=8 and group 4:>8) and average HLA-G concentrations were compared. Samples were grouped according to whether medium sHLA-G was detectable or not. Using Student's t test compared average number of blastomeres per culture well between sHLA-G positive and negative groups. (*) Indicates a significant difference between two groups (t=−2.77, p=0.0061).

Table 10 illustrates the comparison between HLA-G secretion by human embryos and embryo clevage rate.

TABLE 10

Association Between HLA-G Secretion by Human Embryos and Embryo Cleavage Rate

| | Number of Blastomeres | | | |
|---|---|---|---|---|
| | ≦4 (N = 56) | >4–6 (N = 86) | >6–8 (N = 116) | >8 (N = 12) |
| | HLA-G(µg/ml) | | | |
| Median | 0.104 | 0.190 | 0.180 | 0.308 |
| 25–75% | 0.049–0.243 | 0.075–0.373 | 0.115–0.376 | 0.149–0.343 |

Samples were grouped according to average number of blastomeres per embryo in each well. Association between sHLA-G concentrations and embryo cleavage rate was analyzed by using Kruskal-Wallis one way analysis of variance on rank. H=15.1 and p=0.0018. It was found that sHLA-G concentrations were significantly different between these groups (Kruskal-Wallis, p=0.0018). sHLA-G concentration was lowest with embryos less than 4 blastomeres and greatest with >8 blastomeres.

Of the total 137 couples, 51 had a live birth, 9 had a spontaneous abortion and 77 did not achieve a pregnancy. Similar to findings from other centers (Ziebe et al., Human reprod 1997; 12:1545–9), the pregnancy rate from embryos with average >6 of cells was tended to be higher than that from embryos with ≦6 cells (40.9% vs 30.6%), but this did not reach statistical significance in our study. For this difference to be significant with a p value of 0.800, a total of 440 subjects would have been required.

Figure 18:
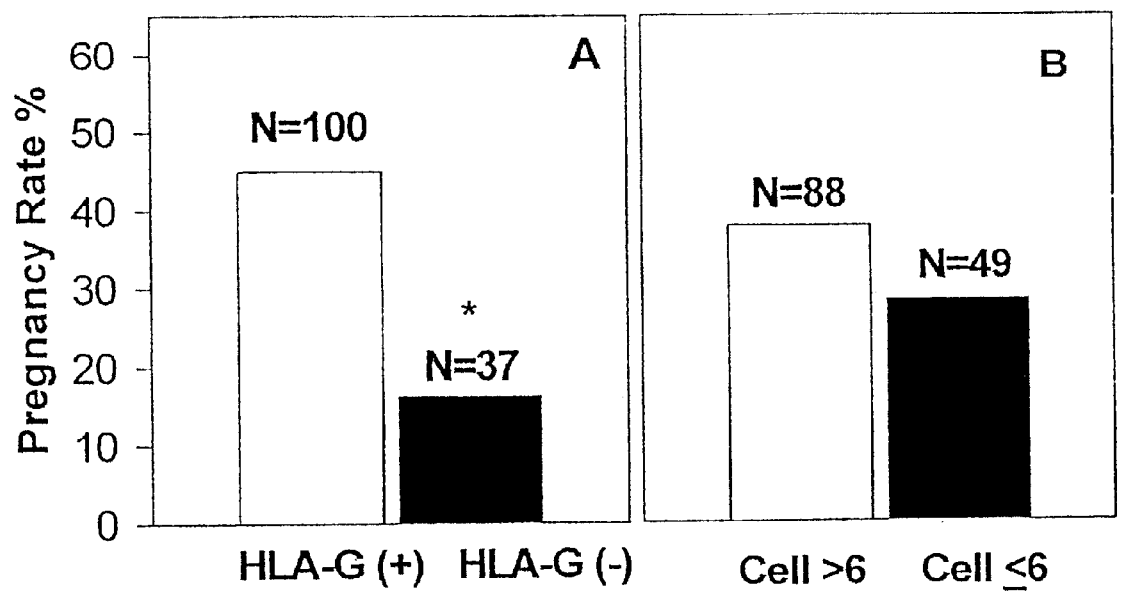
FIG. 18 illustrates pregnancy rates of (A) HLA-G positive and negative groups and (B) groups having average number of blastomeres larger than 6 and less than or equal to 6.

FIG. 18 illustrates the pregnancy rate in patients who had sHLA-G positive embryos transferred was significantly higher than that in patients who received sHLA-G negative embryos (45% vs 16.2%, Chi-square=8.38, p=0.0038). Pregnancy rates were compared between HLA-G positive and negative groups and between average number of blastomeres larger than 6 and less/equal to 6 groups by using Chi-square testing. A significant difference between two HLA-G groups was observed, while no statistical significance was not found between the cell number groups.

HLA-G positivity was a better independent predictor than cleavage rate for successful pregnancy. Of all pregnancy cases 88.8% resulted from transfer of embryos that were HLA-G positive. Only 16.2% of embryos transferred from HLA-G negative wells gave rise to a pregnancy. To determine if prior knowledge of HLA-G detection could have potentially improved pregnancy rates, those cases in which the investigators unknowingly transferred HLA-G negative embryos and froze HLA-G positive embryos were analysed. In total there were 17 cases where this occurred. Only 2/17=11.8% of these cases resulted in a pregnancy.

In order to combine sHLA-G detectability and cleavage rate, all transferred embryos were subdivided into four groups: group I were sHLA-G negative combined with a low cleavage rate (average blastomere≦6); group II were SHLA-G negative combined with a high cleavage rate (average blastomeres>6); group III were sHLA-G positive combined with a low cleavage rate and group IV were sHLA-G positive combined with a high cleavage rate.

Figure 19:
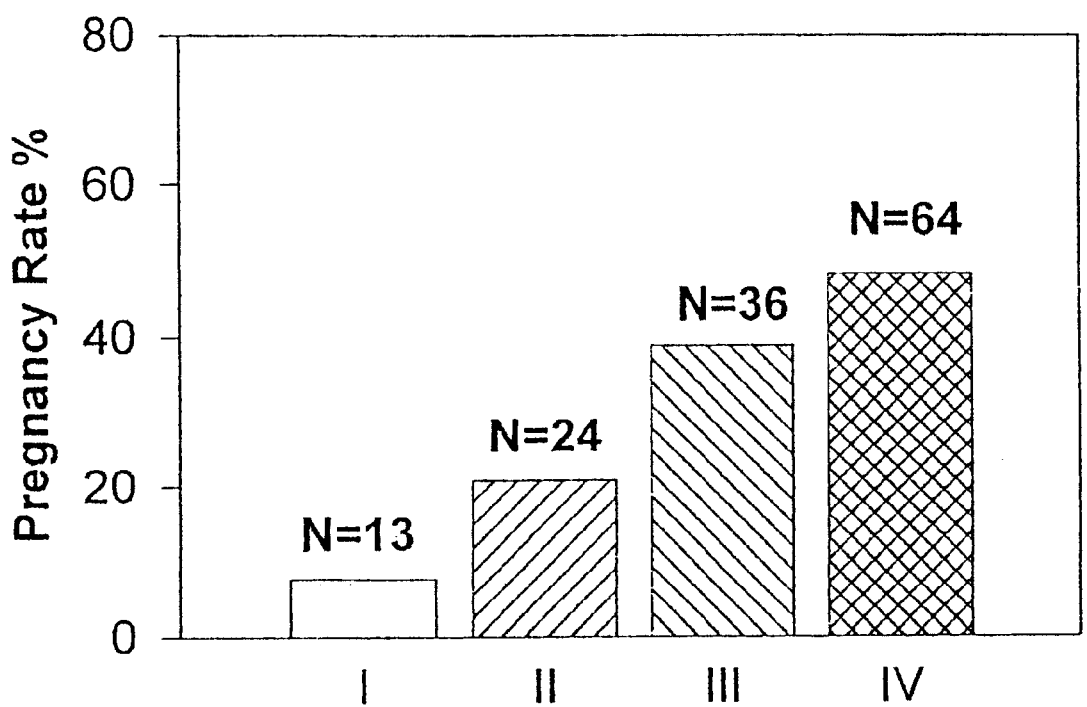
FIG. 19 shows pregnancy rates compared among various groups combining sHLA-G detection and embryo cleavage rate.

FIG. 19 illustrates that differences in pregnancy rate among these groups were statistically significant. The lowest pregnancy rate was seen in the combined HLA-G negative and low cleavage rate group (7.7%) and the highest pregnancy rate was observed in the combined sHLA-G positive and high cleavage rate group (48.4%) (Chi-square=11.1, p=0.0112). Pregnancy rates were compared among various groups combining sHLA-G detection and embryo cleavage rate. Group I: combined sHLA-G=0 and number of blastomeres≦6; group II: sHLA-G=0, number of blastomeres>6; group III: HLA-G>0, number of blastomeres≦6; and group IV: sHLA-G>0, number of blastomeres>6 (Chi-square=11.1, p=0.0112). 3C G4 was shown to be an IgA mAb as determined using an ImmunoType kit (Amersham, Buckinghamshire, England).

Table 11 shows results obtained for patients according to age. As expected, pregnancy rates were higher in women <38 years old as compared to those ≧38 years old. Pregnancy rates were significantly higher in either group if HLA-G was detected in medium from transferred embryos.

TABLE 11

Comparison of Pregnancy Rates by Age and sHLA-G Detection.

| | <38 years old | | | | ≧38 years old | | | |
|---|---|---|---|---|---|---|---|---|
| | HLA-G (+) N = 74 | | HLA-G (−) N = 28 | | HLA-G (+) N = 26 | | HLA-G (−) N = 9 | |
| | N | % | N | % | N | % | N | % |
| Total Pregnant | 43 | 58.1 | 6 | 21.5 | 11 | 42.3 | 0 | 0 |
| Spontaneous Abortion | 6 | 8.1 | 0 | 0 | 3 | 11.5 | 0 | 0 |
| Live Birth | 37 | 50.0 | 6 | 21.5 | 8 | 30.8 | 0 | 0 |

Chi-square = 20.7, p = 0.0021.

Patients were grouped according to their age <38 or ≧38 years. Pregnancy rate was compared among subgroups according to whether HLA-G positive embryos were transferred or not by Chi-square analysis.

Discussion and Conclusions. Embryo secretion of sHLA-G protein is variable. Secretion of HLA-G is correlated with a higher embryo cleavage rate. Embryos secreting soluble HLA-G have a higher IVF pregnancy rate than those lacking HLA-G secretion and detection of sHLA-G was a better prediction of pregnancy outcome than cleavage rate alone. Combined sHLA-G detection and high cleavage rate was the best predictor of IVF outcome.

In vitro fertilization has become one of the most widely used methods for the treatment of human infertility. At present, two main determinants are used for selection of embryos for transfer. Firstly, embryo morphology grading is widely used. Various grading systems by different laboratories are utilized that take into account such factors as cell shape, cell size disparity, fragment percentage, and fragmentation pattern. Secondly, cleavage status before transfer is determined by counting the number of blastomeres present. Both factors have some utility, but are relatively poor predictors of subsequent implantation and pregnancy. Average embryo grade was not predictive of pregnancy in our study agreeing with many other reports (Grimbizis et al. Human Reprod 1998; 13: 884–9). Pregnancy rate tended to be higher with a higher average cleavage rate, but this did not reach statistical significance.

Using the specific and sensitive ELISA according to the invention, this study demonstrated that some pre-implantation embryos secrete HLA-G. This finding supports previous uses of ICC to detect membrane bound and intracellular HLA-G (Jurisicova et al., *Proc. Nat. Acad. Sci. USA.* 1996; 93:161–5). The soluble HLA-G detected by the ELISA according to the invention could be either the form in which a post transcriptional mRNA modification results in deletion of the transmembrane portion of HLA-G, or by proteolytic cleavage of a membrane bound form, or both. In this study, we found no association between sHLA-G detection and embryo morphology.

A positive correlation was found between sHLA-G concentrations and embryo cleavage rate. Since it has been reported that the Ped gene and its product the Qa-2 antigen influence the cleavage rate of mouse embryos, HLA-G could be a functional homologue of the Qa-2 antigen, proposed by Cao et al. (*Mol Human Reprod.* 1999; 5: 541–7). Therefore, sHLA-G, which is secreted by embryos could enhance embryo development. This could also be an explanation for why cleavage rate is improved when embryos are cultured in groups.

A positive association exists between HLA-G expression in sibling embryos and implantation after IVF. In this study, sHLA-G was measured in culture medium from embryos before uterine transfer. This provided a means for directly detecting any association between HLA-G produced by the embryos actually transferred and pregnancy outcome. In this study we demonstrated that transferred embryos which secrete detectable levels of HLA-G give rise to a significantly higher pregnancy rate than those which were HLA-G negative. The combination of a positive sHLA-G test and a higher cleavage rate gave rise to the highest pregnancy rate. Therefore, advantageously, these two tests combined could be used to select embryos more likely to result in a pregnancy. The data was further analysed to see if there were cases in which this test alone would have changed the decision of which embryos to transfer. There were 2 pregnancies out of 17 cases (11.8%) in which the embryos transferred were sHLA-G negative and the spare embryos that were frozen were HLA-G positive. Therefore, transferring the sHLA-G positive embryos in this group may have resulted in a higher pregnancy rate.

In addition to the potential role of HLA-G in improving embryo cleavage rate, as discussed above, sHLA-G may also play a role in communication with the maternal immune system to prevent rejection of transferred embryos. This hypothesis is supported by the findings that higher pregnancy rates resulted from embryos with detectable sHLA-G even when the cleavage rate was low and by observations that purified HLA-G prevented the generation of an allo-response in vitro.

In summary, this study demonstrates variable detection of sHLA-G in human embryo culture conditioned medium by the ELISA for HLA-G according to the invention. A significantly higher pregnancy rate is observed when embryos that secrete sHLA-G are transferred. Secretion of HLA-G was a better independent predictor of pregnancy rate than cleavage status alone. Finally, combining sHLA-G detection and cleavage rate was the best overall predictor of IVF pregnancy outcome.

EXAMPLE 6

Preparation of a Miniaturized HLA-G Detection Assay

As shown in Example 5, pregnancy outcomes from transferred embryos testing positive for sHLA-G secretion are significantly better than those with undetectable sHLA-G. Thus, to ascertain whether an embryo to be transferred has an increased likelihood of leading to pregnancy, an HLA-G detection assay can be conducted. The ELISA according to the invention is adapted to a miniaturized HLA-G detection assay which advantageously can be used in a clinical setting. Such a miniaturized assay provides a rapid quantitative measurement of HLA-G secreted into a medium in which an embryo is incubated, without requiring that a sample be sent off for laboratory analysis.

A polystyrene chip is prepared by coating with 3C/G4 antibody according to the invention to form an active region. A 10 µl sample of embryo incubation medium is placed on the active region of the chip. HLA-G is detected using HRP-2C/C8 conjugate, according to the invention, by inserting the chip containing the sample into a hand-held reader, as disclosed in International Patent Application No. PCT/CA99/01079, to Peter Lea, published as International Publication No. WO 00/29847 on May 25, 2000. This document is incorporated herein by reference in its entirety.

A fluorescent end-point is used to detect binding of antibodies, indicative of the presence of HLA-G. Advantageously, in an optional embodiment, the chip allows separation of fluid from non-fluid components of a sample. The device is a point-of-care device, which may be used in a clinical setting. The data is electronically collected and/or transmitted for further evaluation.

EXAMPLE 7

Preparation of a Cancer Screening Kit

HLA-G secretion from various cell types may be indicative of cancer. Certain cancerous states, such as breast cancer, can be screened using a kit according to the invention. Thus, to ascertain whether a tissue sample may be cancerous or has potential to become cancerous, an HLA-G detection assay can be conducted. The appropriate tissue sample is collected, in this case from a breast tissue biopsy. Cells from the biopsy may be used as primary culture, or the sample may be homogenized according to methods disclosed herein with reference to placental tissue.

An ELISA is prepared by coating a support with 3C/G4 antibody. A 100 µl sample of homogenized tissue is placed on the coated support. HLA-G is allowed time to bind to the support, washed, and an aliquot of a HRP-2C/C8 conjugate is placed thereon. The conjugate binds to HLA-G remaining on the support. A non-cancerous standard, such as a known value, or a value previously determined in the same individual from a previous non-cancerous biopsy is used to compare with the sample value of HLA-G. Threshold values of HLA-G indicative of cancerous and non-cancerous states are used for comparison with values measured in the tissue sample.

All references noted herein are incorporated by reference. The foregoing examples are merely indicative of embodiments of the invention, and should in no way be construed as limiting.

What is claimed is:

1. Hybridoma 2C/C8 deposited at the International Depositary Authority of Canada on Sep. 13, 2000 having IDAC Accession Number IDAC 130900-1.

2. An anti-HLA-G antibody from the hybridoma of claim 1.

3. Hybridoma 3C/G4 deposited at the International Depositary Authority of Canada on Sep. 13, 2000 having IDAC Accession Number IDAC 130900-2.

4. An anti-HLA-G antibody from the hybridoma of claim 3.

5. A method for identifying pre-eclampsia, an HLA-G (human leucocyte antigen G) indicative condition, in a patient comprising the steps of:

a) obtaining a biological sample from the patient;

b) depositing the biological sample on a support having an immobilized anti-HLA-G antibody bound thereto; said immobilized anti-HLA-G antibody binding to a first region of HLA-G, and being selected from the group consisting of 2C/C8 from 2C/C8 hybridoma deposited as IDAC Accession Number 130900-1 on Sep. 13, 2000 and 3C/G4 from 3C/G4 hybridoma deposited as IDAC Accession Number 130900-2 on Sep. 13, 2000;

c) contacting the support having the biological sample deposited thereon with an HLA-G label, said label binding to a second region of HLA-G and comprising a mobile anti-HLA-G antibody having a reporter molecule bound thereto; said mobile anti-HLA-G antibody being selected from the group consisting of 2C/C8 and 3C/G4, provided that only one of said mobile anti-HLA-G antibody and said immobilized anti-HLA-G antibody is 2C/C8;

d) removing unbound HLA-G label;

e) detecting bound HLA-G label;

f) comparing the bound HLA-G label detected in step (e) to a standard, to quantify HLA-G in the sample;

g) comparing HLA-G in the sample quantified in step (f) to a level of HLA-G indicative of pre-eclampsia; and h) identifying pre-eclampsia in a patient having a quantity of HLA-G in the sample indicative of pre-eclampsia.

6. A method for determining potential for successful implantation of an embryo comprising the steps of:

a) obtaining a sample of a fluid medium incubating said embryo;

b) depositing the sample on a support having an immobilized anti-HLA-G (human leucocyte antigen G) antibody bound thereto; said immobilized anti-HLA-G antibody binding to a first region of HLA-G, and being selected from the group consisting of 2C/C8 from 2C/C8 hybridoma deposited as IDAC Accession Number 130900-1 on Sep. 13, 20001 and 3C/G4 from 3C/G4 hybridoma deposited as IDAC Accession Number 130900-2 on Sep. 13, 2000;

c) contacting the support having the sample deposited thereon with an HLA-G label, said label binding to a second region of HLA-G and comprising a mobile anti-HLA-G antibody having a reporter molecule bound thereto; said mobile anti-HLA-G antibody being selected from the group consisting of 2C/C8 and 3C/G4, provided that only one of said mobile anti-HLA-G antibody and said immobilized anti-HLA-G antibody is 2C/C8;

d) removing unbound HLA-G label;

e) detecting bound HLA-G label;

f) comparing the bound HLA-G label detected in step (e) to a standard, to quantify HLA-G in the sample;

g) comparing HLA-G in the sample quantified in step (f) to a level of HLA-G indicative of successful implantation of an embryo; and h) determining potential for successful implantation of said embryo having a quantity of HLA-G in the sample indicative of potential success.

7. A method for selecting an embryo for in vitro fertilization (IVF) by detecting soluble HLA-G (human leucocyte antigen G) secreted by the embryo into an incubation medium comprising the steps of:

a) depositing a sample of the embryo incubation medium on a support having an immobilized anti-HLA-G antibody bound thereto; said immobilized anti-HLA-G antibody binding to a first region of HLA-G, and being selected from the group consisting of 2C/C8 from 2C/C8 hybridoma deposited as IDAC Accession Number 130900-1 on Sep. 13, 2000 and 3C/G4 from 3C/G4 hybridoma deposited as IDAC Accession Number 130900-2 on Sep. 13, 2000;

b) contacting the support having the sample deposited thereon with an HLA-G label, said label binding to a second region of HLA-G and comprising a mobile anti-HLA-G antibody having a reporter molecule bound thereto; said mobile anti-HLA-G antibody being selected from the group consisting of 2C/C8 and 3C/G4, provided that only one of said mobile anti-HLA-G antibody and said immobilized anti-HLA-G antibody is 2C/C8;

c) removing unbound HLA-G label;

d) detecting bound HLA-G label;

e) comparing the bound HLA-G label detected in step d) to a standard, to quantify HLA-G in the sample; and f) selecting the embryo for IVF if the embryo secreted soluble HLA-G at a minimum of 0.01 $\mu$g/ml into the sample of incubation medium.

* * * * *

UNITED STATES PATENT AND TRADEMARK OFFICE
CERTIFICATE OF CORRECTION

PATENT NO. : 6,613,538 B2
DATED : September 2, 2003
INVENTOR(S) : Clifford L. Librach et al.

It is certified that error appears in the above-identified patent and that said Letters Patent is hereby corrected as shown below:

<u>Title page,</u>
Item [57], ABSTRACT,
Line 9, delete "an".

<u>Column 3,</u>
Line 13, "American" should be -- America --.
Line 60, "al" should be -- α 1 --.

<u>Column 4,</u>
Line 10, before "object" insert -- an --.
Line 10, "intention" should be -- invention --.
Line 41, "an" should be -- on --.

<u>Column 5,</u>
Line 1, "binding" should be -- binds --.
Line 8, "agents" should be -- agent --.

<u>Column 6,</u>
Line 65, "an" should be -- a --.

<u>Column 9,</u>
Line 56, "(996)" should be -- (1996) --.
Line 57, "USA." should be -- U.S.A. --.

<u>Column 11,</u>
Line 2, "4H/84" should be -- 4H84 --.

<u>Column 15,</u>
Line 62, "it's" should be -- its --.

<u>Column 17,</u>
Line 20, "β2-microglobumin" should be -- β2-microglobulin --.
Line 60, "(Fisher et a.)" should be -- (Fisher et al.) --.

<u>Column 18,</u>
Line 25, "w as" should be -- was --.
Line 49, "490 run" should be -- 490 nm --.

<u>Column 19,</u>
Line 8, "10 ng/ml" should be -- 10 mg/ml --.

UNITED STATES PATENT AND TRADEMARK OFFICE
CERTIFICATE OF CORRECTION

PATENT NO.     : 6,613,538 B2
DATED          : September 2, 2003
INVENTOR(S)    : Clifford L. Librach et al.

It is certified that error appears in the above-identified patent and that said Letters Patent is hereby corrected as shown below:

<u>Column 20,</u>
Line 67, "Th1-type" should be -- Th2-type --.

<u>Column 23,</u>
Line 4, "Imnunol" should be -- Immunol --.
Line 58, "as" should be -- is --.

<u>Column 24,</u>
Line 64, "St. Louis, MD," should be -- St. Louis, MO, --.

<u>Column 25,</u>
Line 1, "St. Louis, MD," should be -- St. Louis, MO, --.
Line 10, "Elisa" should be -- ELISA --.
Line 49, "HLA-G (+), N = 116" should be -- HLA-G (–), N = 116 --.

<u>Column 27,</u>
Line 8, "3C G4" should be -- 3C/G4 --.

<u>Column 30,</u>
Line 39, "20001" should be -- 2000 --.

Signed and Sealed this

Third Day of February, 2004

JON W. DUDAS
*Acting Director of the United States Patent and Trademark Office*